United States Patent [19]
Wright et al.

[11] Patent Number: 5,623,930
[45] Date of Patent: Apr. 29, 1997

[54] ULTRASOUND SYSTEM FOR FLOW MEASUREMENT

[75] Inventors: J. Nelson Wright, Menlo Park; Donald R. Langdon, Mountain View; Ismayil M. Guracar, Redwood City, all of Calif.

[73] Assignee: Acuson Corporation, Mountain View, Calif.

[21] Appl. No.: 432,858

[22] Filed: May 2, 1995

[51] Int. Cl.$^6$ ................................. A61B 8/06
[52] U.S. Cl. ........................ 128/661.1; 128/660.09
[58] Field of Search ................. 128/660.04, 660.05, 128/661.07–661.1; 73/861.25; 364/413.25

[56] References Cited

U.S. PATENT DOCUMENTS

| | | | |
|---|---|---|---|
| 4,067,236 | 1/1978 | Hottinger | 128/661.1 |
| 4,103,679 | 8/1978 | Aronson | 128/661.1 |
| 4,265,126 | 5/1981 | Papadofrangakis et al. | 73/861.25 |
| 4,373,533 | 2/1983 | Iinuma | 128/660.05 |
| 4,476,874 | 10/1984 | Taenzer et al. | 128/660.05 |
| 4,509,526 | 4/1985 | Barnes et al. | 128/661.1 |
| 4,790,322 | 12/1988 | Iinuma | 128/661.1 |
| 4,873,985 | 10/1989 | Nakajima | 128/661.09 |
| 4,928,698 | 5/1990 | Bonnefous | 128/661.09 |
| 5,014,710 | 5/1991 | Maslak et al. | 128/660.05 |
| 5,062,427 | 11/1991 | Seo et al. | 128/661.1 |
| 5,165,413 | 11/1992 | Maslak et al. | 128/660.05 |
| 5,195,521 | 3/1993 | Melton, Jr. et al. | 128/660.02 |
| 5,235,984 | 8/1993 | D'Sa | 128/660.07 |
| 5,280,787 | 1/1994 | Wilson et al. | 128/661.1 |
| 5,322,067 | 6/1994 | Prates et al. | 128/661.1 X |
| 5,471,990 | 12/1995 | Thirsk | 128/661.09 |
| 5,505,204 | 4/1996 | Picot et al. | 128/661.1 |
| 5,515,857 | 5/1996 | Tsujino et al. | 128/661.1 |

OTHER PUBLICATIONS

"Approximate Quantification of Detected Fractional Blood Volume and Perfusion From 3–D Color Flow and Doppler Power Signal Imaging", P.L. Carson et al., *1993 Ultrasonics Symposium*, pp. 1023–1026.

"Doppler Ultrasound Physics, Instrumentation, and Clinical Applications," by D.H. Evans et al., John Wiley & Sons, New York, Chapter 11, pp. 188–205, 1989.

"Time Domain Formulation of Pulse Doppler Ultrasound and Blood Velocity Estimation by Cross–Correlation," by Bonnefous et al., *Ultrasonic Imaging*, 8, 73–85 (1986).

"Quantitative Measurement of Volume Flow Rate (Cardiac Output) by the Multibeam Doppler Method", H. Tsujino et al., *Journal of the American Society of Echocardiography*, vol. 8, No. 5, Pt. 1, Sep.–Oct. 1995, pp. 621–630.

"Angle Independent Doppler Color Imaging: Determination of Accuracy and a Method of Display," by D. Fei, et al., *Ultrasound in Med. & Biol.*, vol. 20, No. 2, pp. 147–155, 1994.

*Primary Examiner*—Francis Jaworski
*Attorney, Agent, or Firm*—Majestic, Parsons, Siebert & Hsue

[57] ABSTRACT

An ultrasonic transducer is rotated until the displayed vessel has the smallest area. The transducer is then tilted to various angles with respect to a normal to a surface to obtain area and velocity measurements of fluid flow inside a vessel in a body imaged. A least mean square error calculation is then performed to find the area and velocity that will minimize such error. The product of these two quantities is the estimated flow.

61 Claims, 11 Drawing Sheets

Microfiche Appendix Included
(5 Microfiche, 225 Pages)

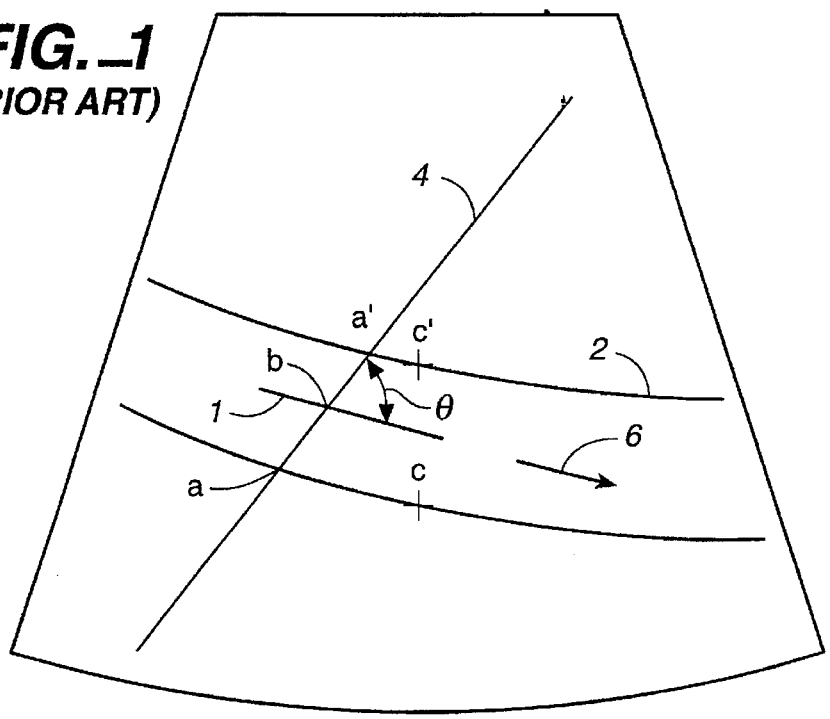
FIG._1
(PRIOR ART)
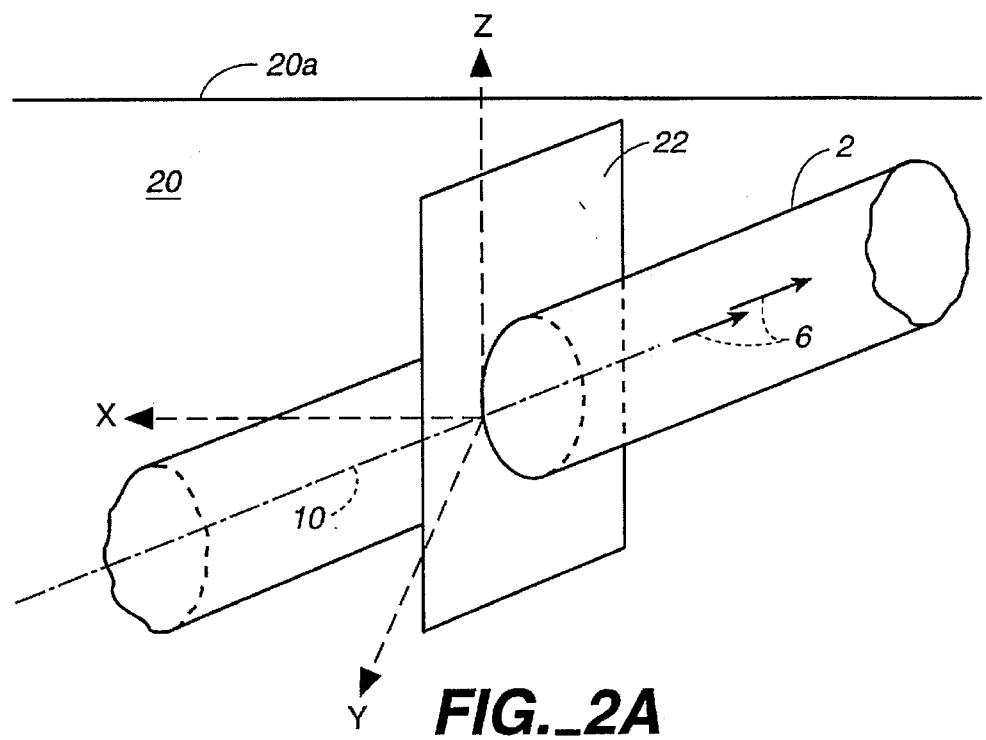
FIG._2A

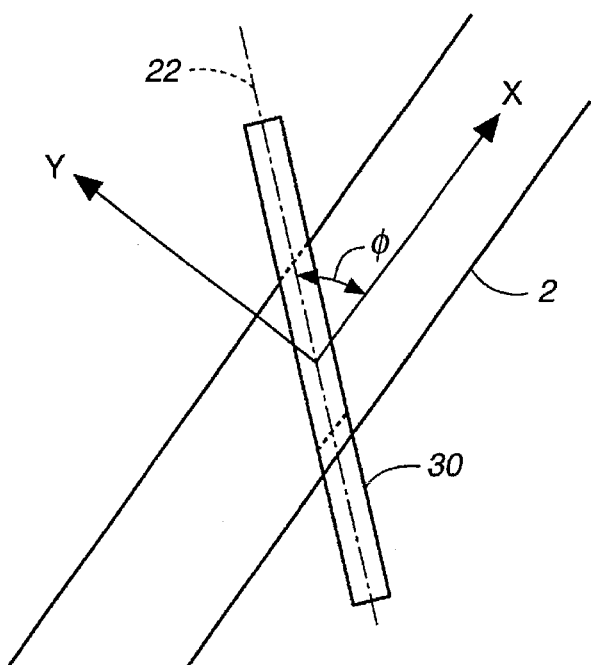
FIG._2B
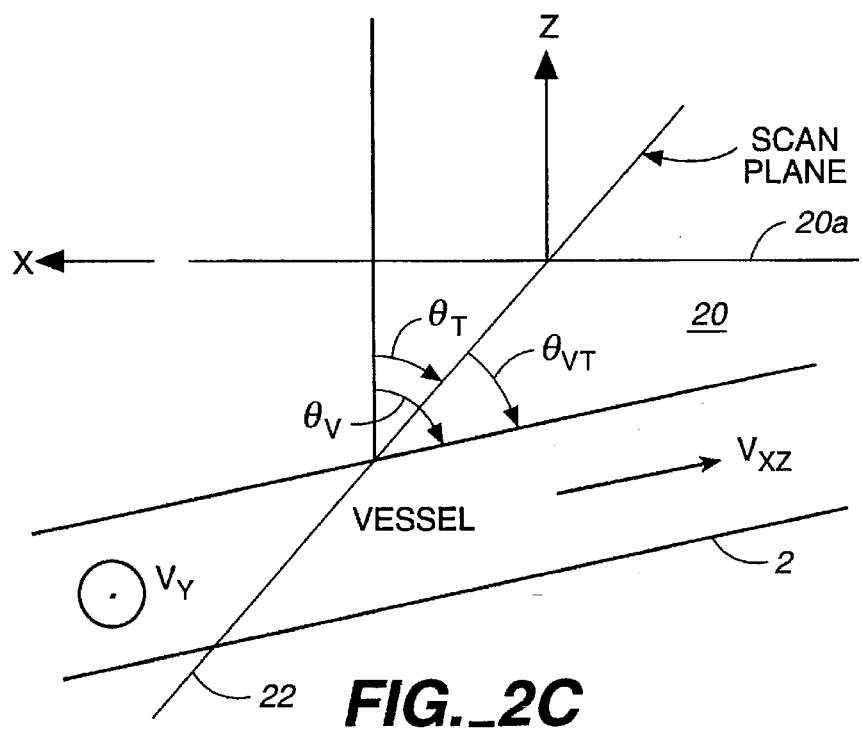
FIG._2C

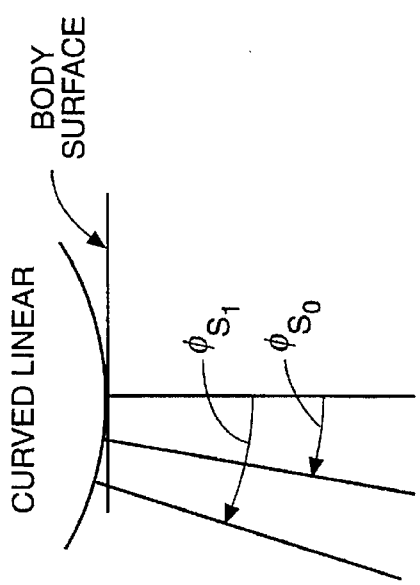
FIG._2D VECTOR FORMAT
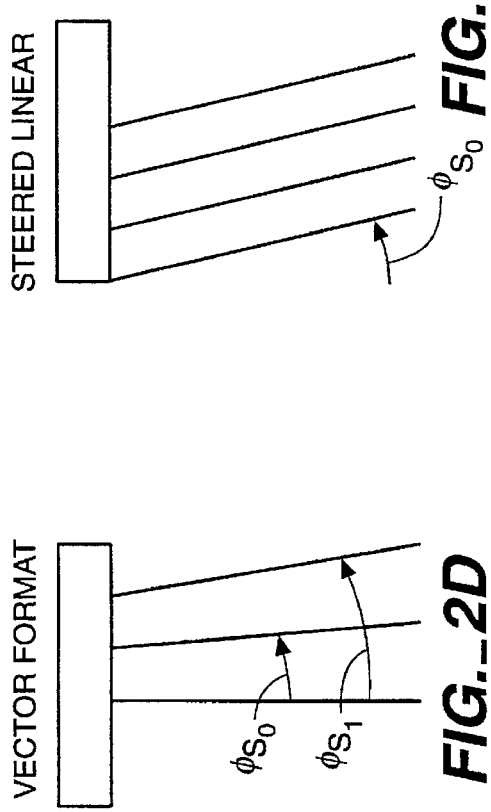
FIG._2E STEERED LINEAR
FIG._2F CURVED LINEAR
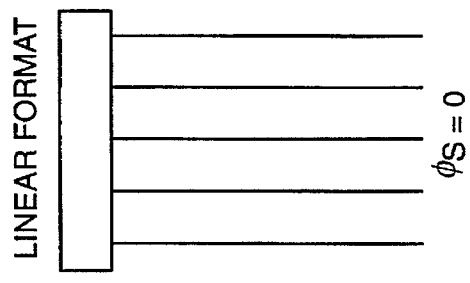
FIG._2G LINEAR FORMAT
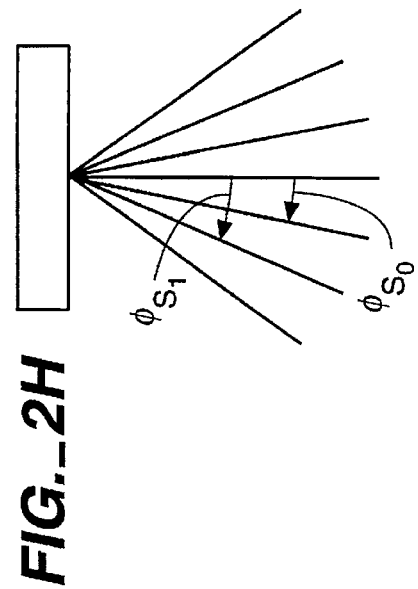
FIG._2H

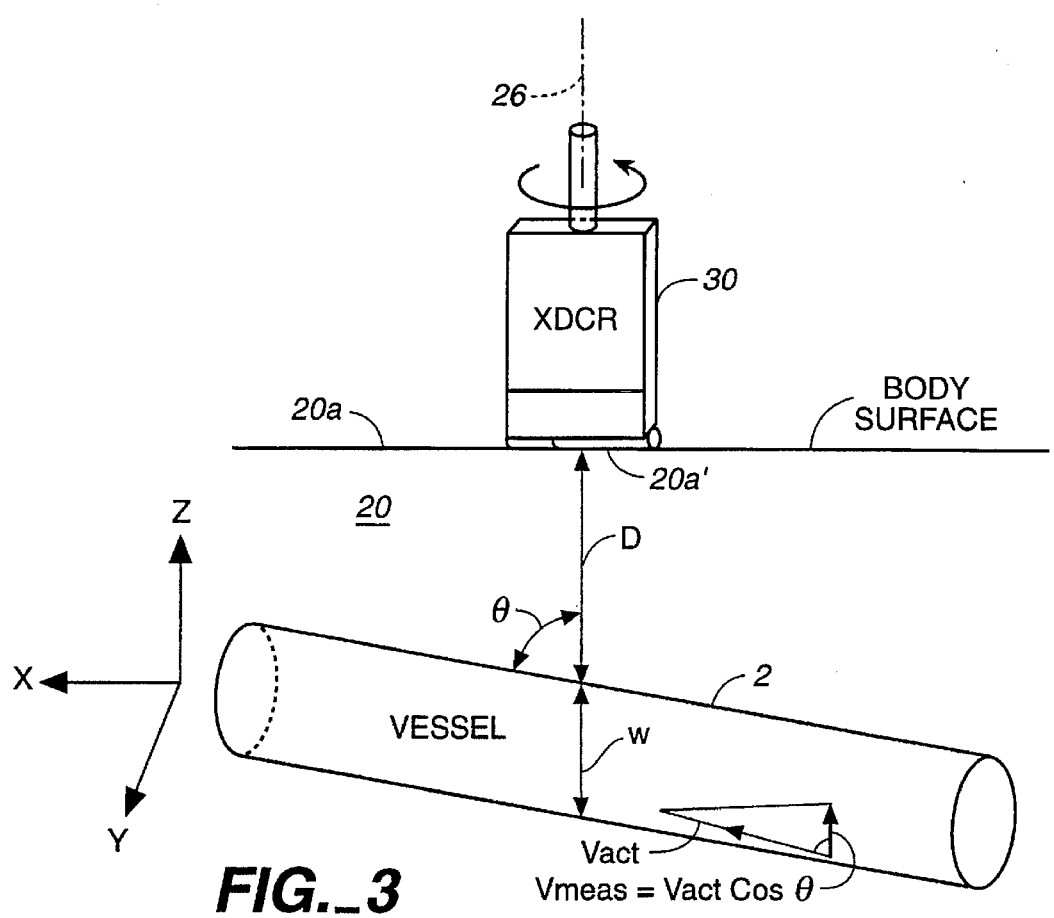
FIG._3
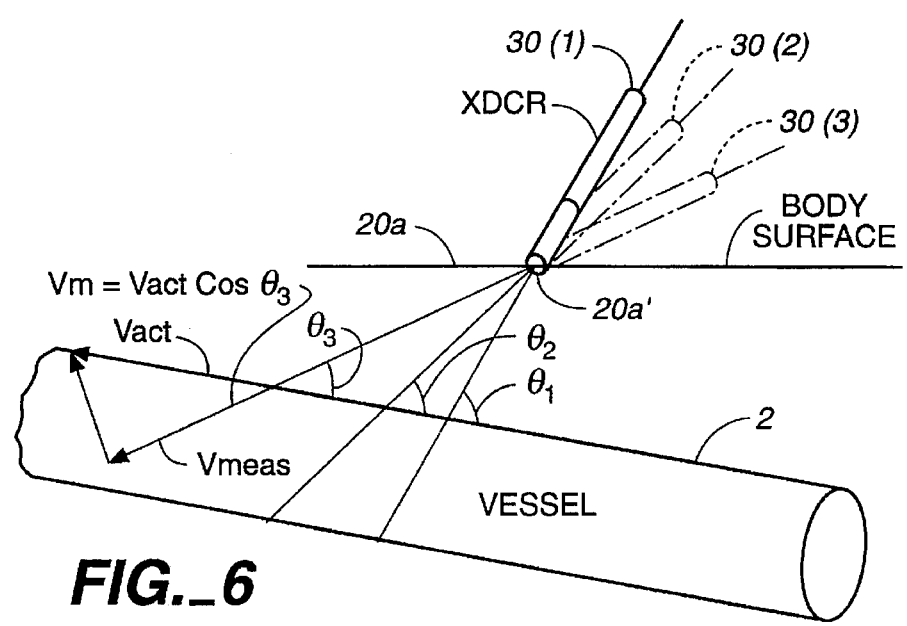
FIG._6

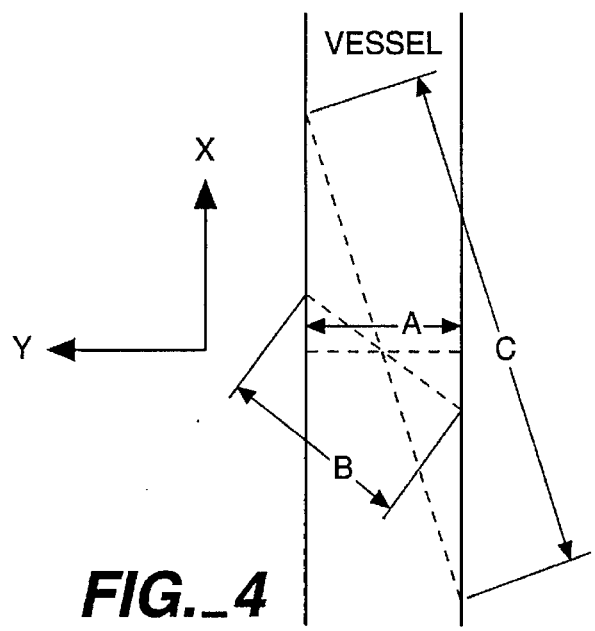
FIG._4
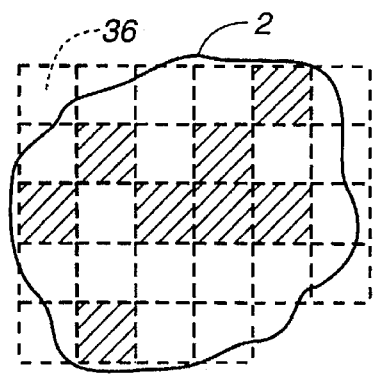
FIG._7
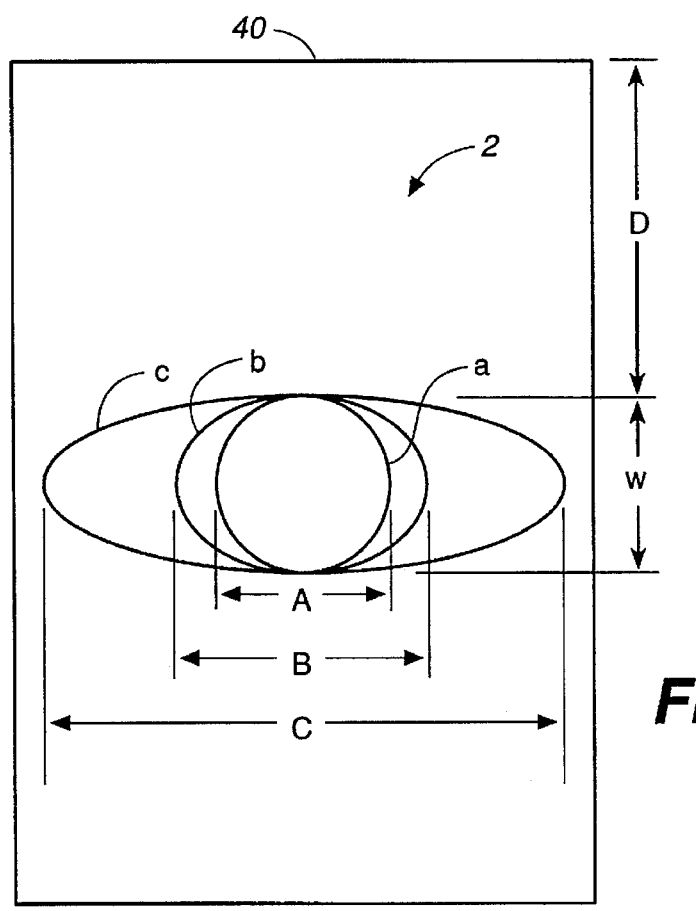
FIG._5

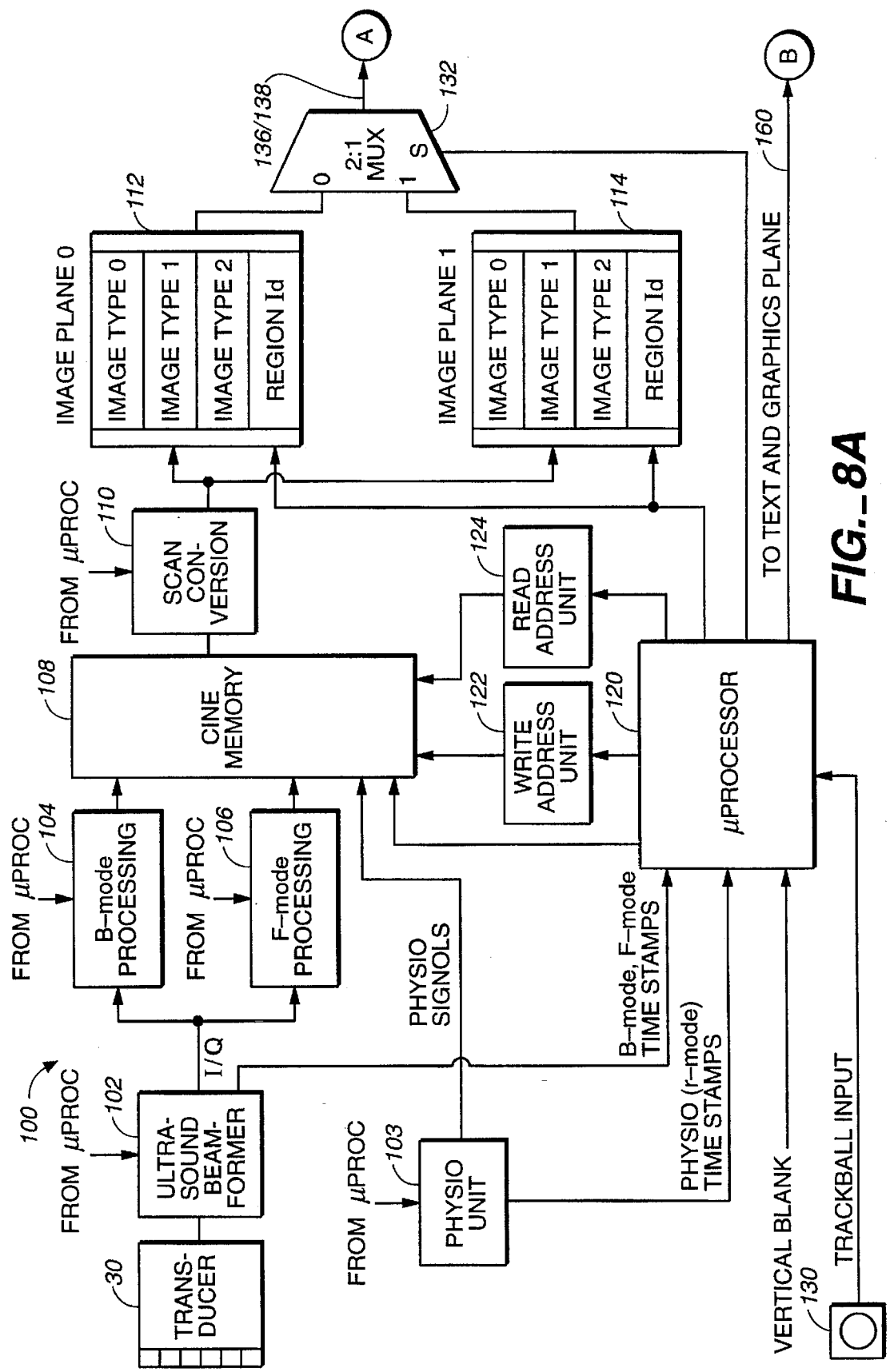

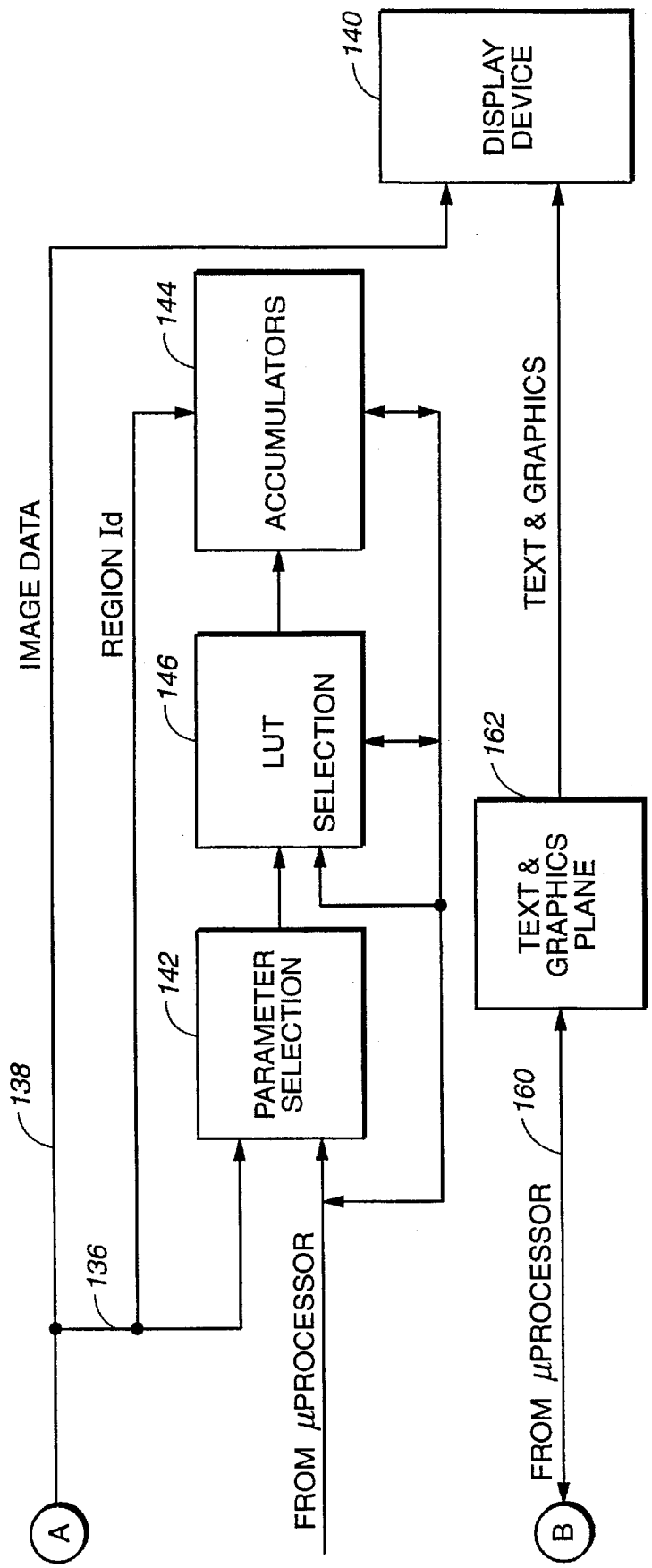

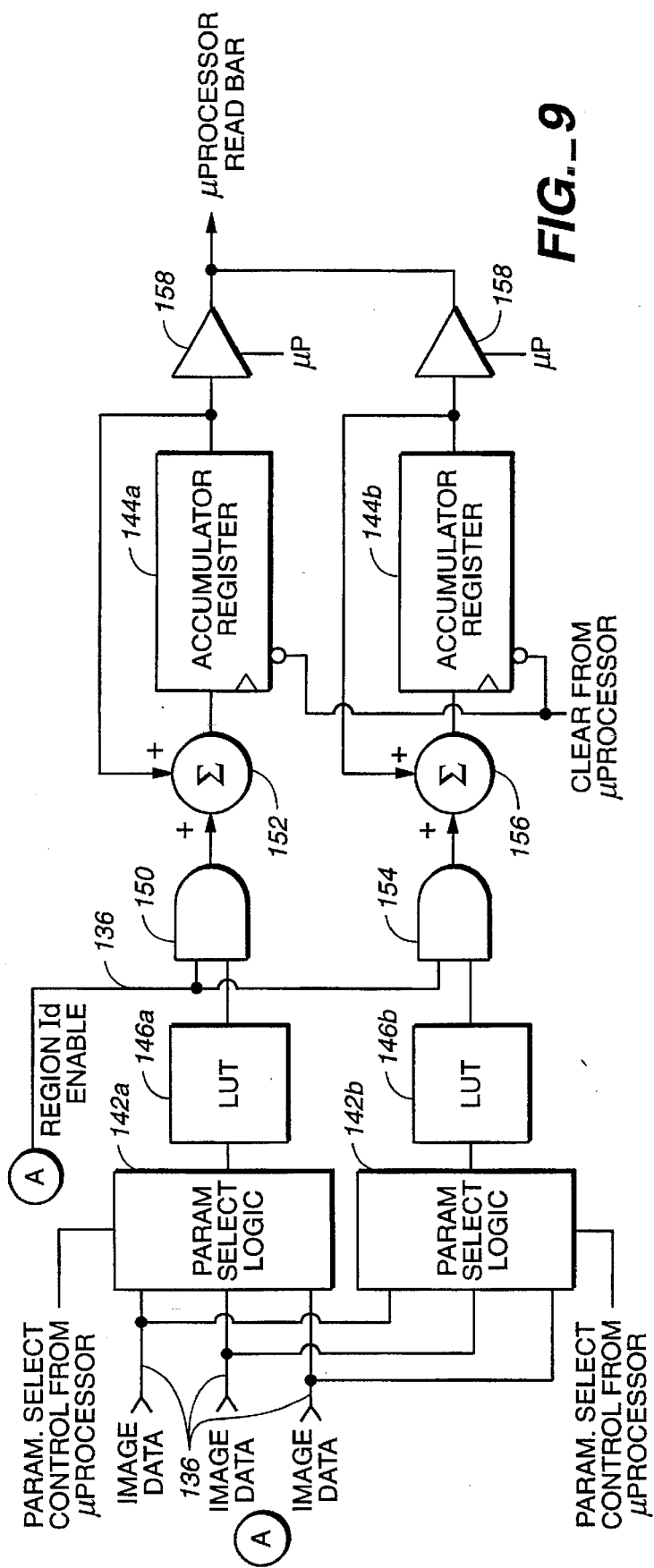
FIG._9
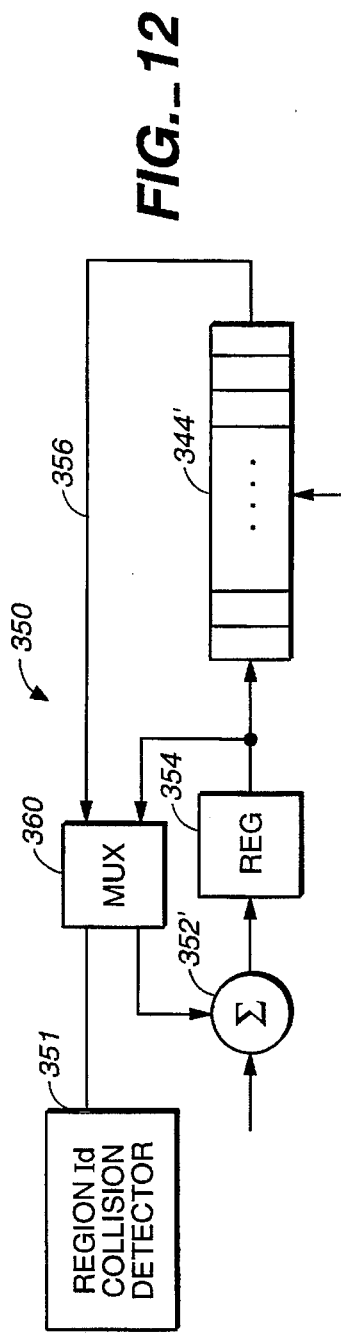
FIG._12

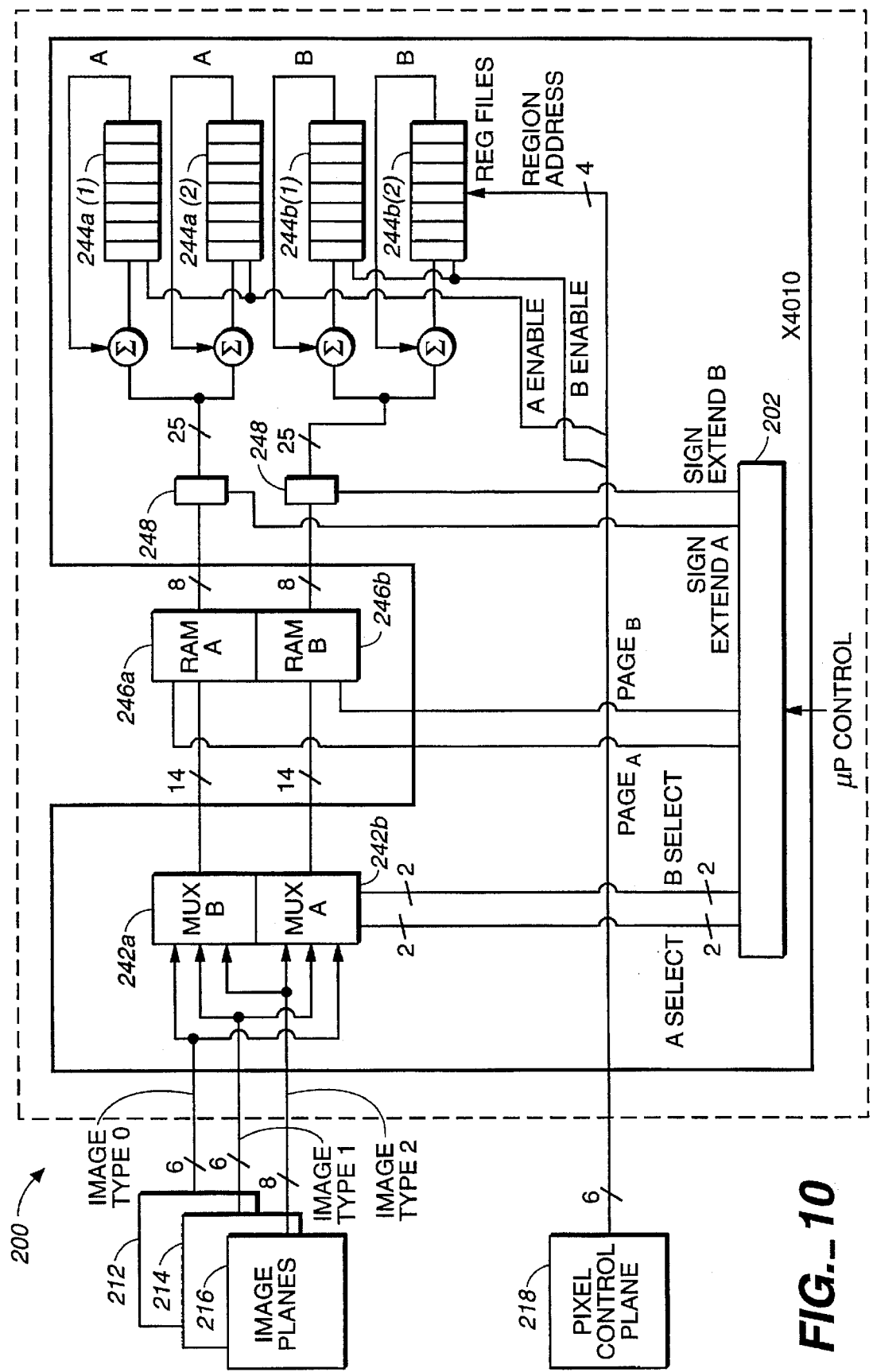
FIG._10

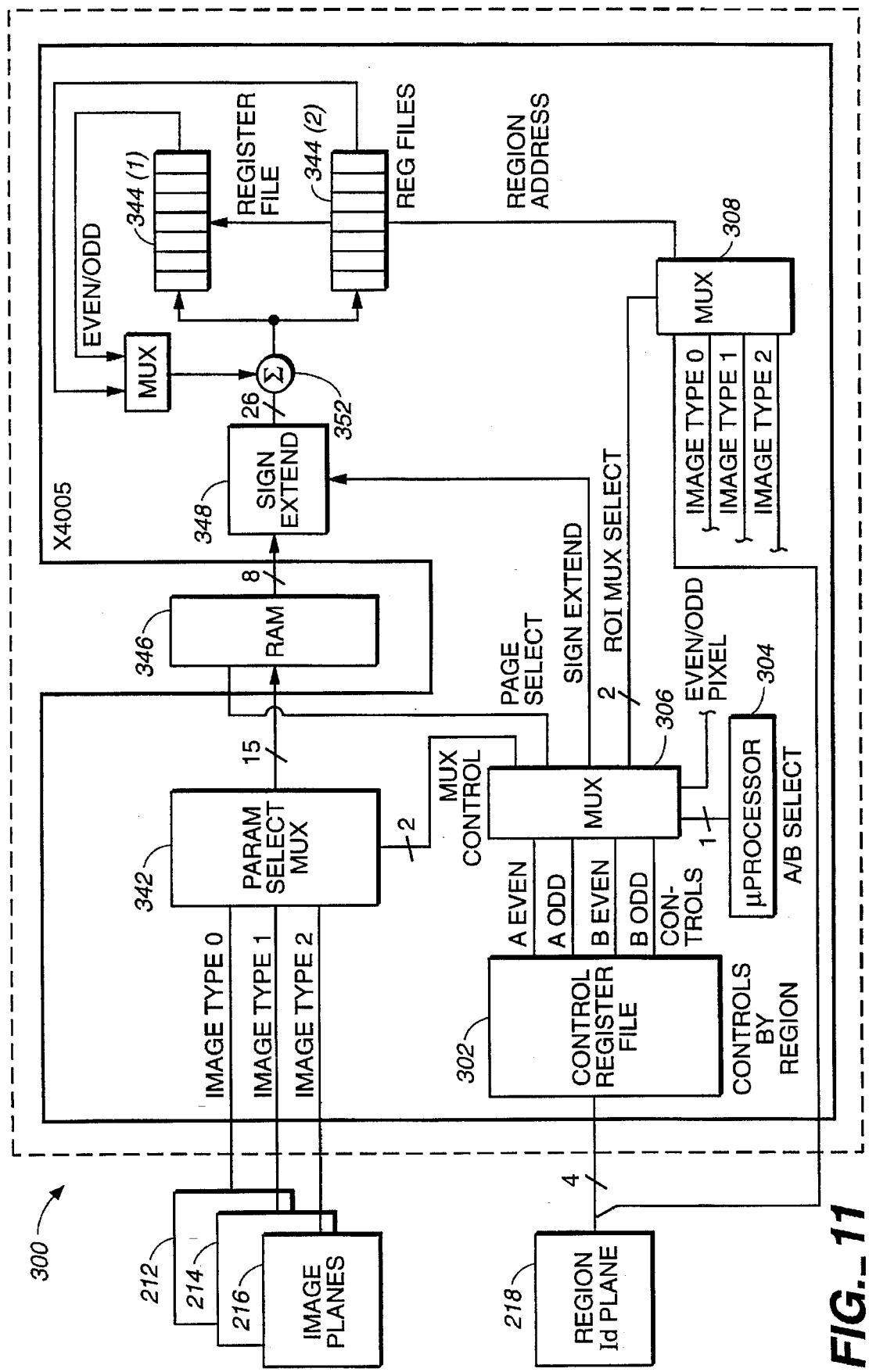
FIG._11

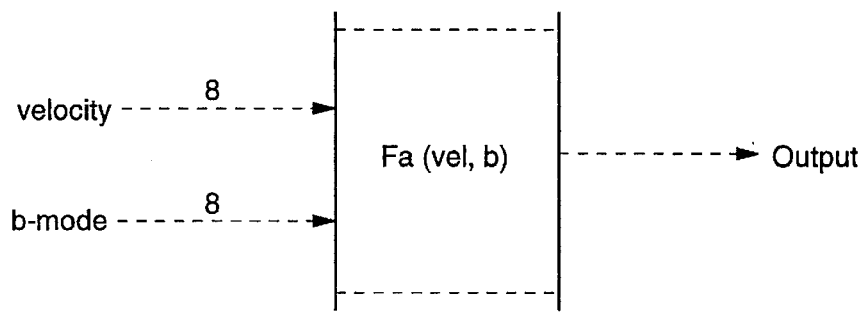
FIG._13
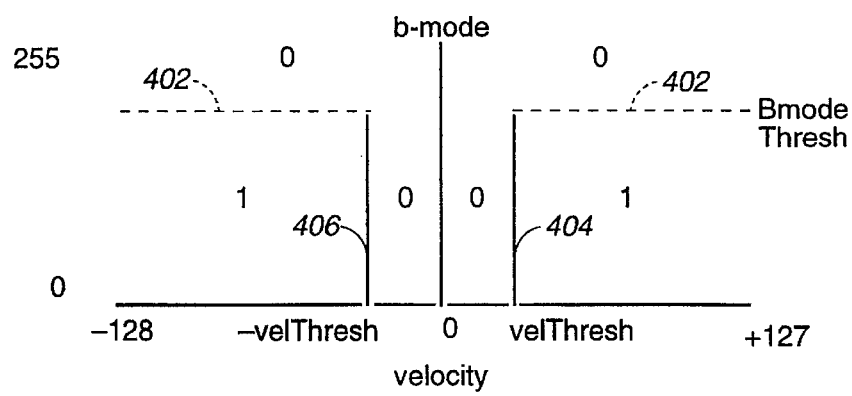
FIG._14
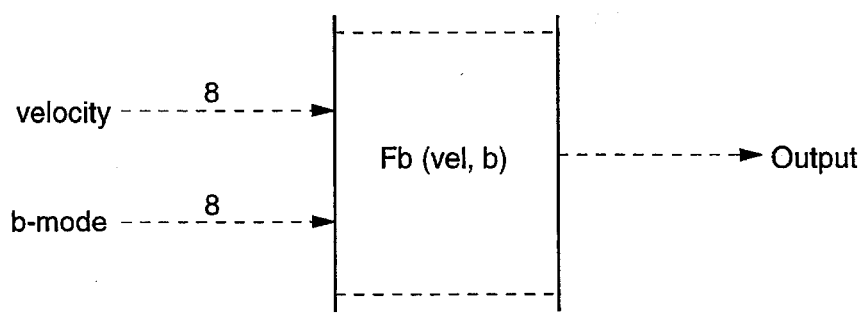
FIG._15
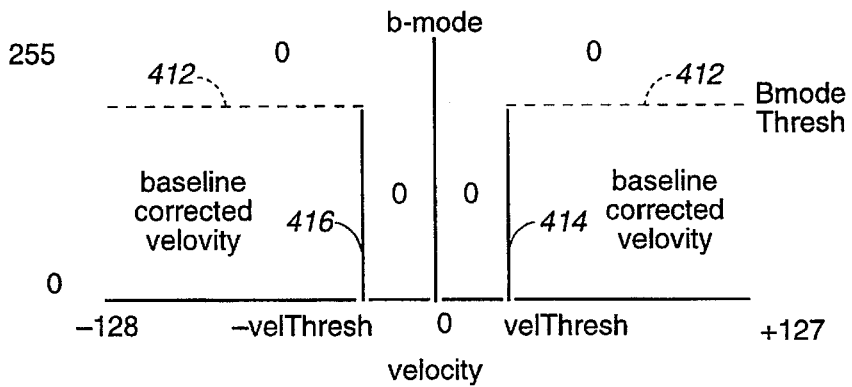
FIG._16

ULTRASOUND SYSTEM FOR FLOW MEASUREMENT

MICROFICHE APPENDICES

This application includes two microfiche appendices (for Implementations 1 and 2). Implementation 1 contains 21 frames and Implementation 2 contains 204 frames.

BACKGROUND OF THE INVENTION

This invention relates in general to ultrasound systems, and in particular to an ultrasound system for measuring fluid flow.

Volume flow measurement in medical ultrasound may be important for medical diagnosis. The volume flow may indicate blockage in blood vessels and performance of diseased or transplanted organs. Thus it may be important to determine whether the blood flow out of a kidney has increased or decreased from the previous week.

At present, accurate measurements of blood flow are not attainable on a real-time basis without the use of invasive procedures. Because of the risks involved, these procedures are usually not used to monitor patients on a continuing basis.

Non-invasive ultrasound techniques for measuring volumetric blood flow have been described in "Doppler Ultrasound Physics, Instrumentation, and Clinical Applications," by D. H. Evans et al., John Wiley & Sons, New York, Chapter 11, pages 188–205, 1989. FIG. 1 is a simplified representation of FIG. 11.1 of Evans et al. and illustrates the techniques described by Evans et al. FIG. 1 illustrates an image of an artery showing the placement of the sample gate a and a', the cursor b used to measure the angle between the axis 1 of vessel 2 and the ultrasound beam 4 and the cursors c and c' used to measure the vessel diameter. As shown in FIG. 1, by orienting the scan plane of the ultrasound transducer in the plane that intersects the blood vessel 2 along the length of the vessel, a gray-scale B-mode image of the vessel on the scan plane is obtained as shown in FIG. 1. A cross-sectional dimension of the blood vessel 2 can be obtained by measuring the distance between c' and c. Then assuming that vessel 2 has a circular cross-section, the cross-sectional area of the vessel can be calculated. An ultrasound scan line 4 intersects vessel 2 and a value for the component of the velocity of blood flow 6 in the direction of the scan line 4 can then be obtained from the ultrasound measurement. The real velocity of blood flow can only be determined if the angle $\theta$ between the scan line 4 and the blood flow direction 6 is known. As taught by Evans et al., assuming that blood flow 6 is along the vessel axis 1, this can be determined from the B-mode image in FIG. 1 by measuring the angle between scan line 4 and a representative axis of vessel 2 to obtain the angle $\theta$.

As noted by Evans et al., however, the above-described method can result in large errors under unfavorable circumstances. For example, the blood vessel may not have a circular cross-section. Furthermore, the blood flow may not have uniform velocity across its cross-section so that the velocity at the center of the vessel is higher than at the periphery. This means that if a narrow ultrasound beam is used to measure the velocity at the center of the vessel and this measured velocity is taken as the mean velocity, this can lead to an overestimation of the mean velocity of blood flow.

None of the above-described conventional methods for measuring blood flow is entirely satisfactory. It is therefore desirable to provide an improved ultrasound system for measuring blood flow.

SUMMARY OF THE INVENTION

This invention is based on the observation that by actually measuring the blood flow velocity at a number of locations substantially across the blood vessel to obtain an averaged velocity and by actually adding or integrating areas associated with received ultrasound signals to obtain a cross-section of the vessel, more accurate values of the blood flow velocity and the cross-section of the blood vessel can be obtained as compared to conventional methods. In the preferred embodiment, the angular dependence (such as $\theta$ in FIG. 1) described above can be eliminated by taking multiple measurements with scan planes at different angles to the blood vessel.

As used in this application, the term "vessel" means an enclosed region or zone in a body that permits fluid flow therein. In this application, the term "the actual cross-sectional area of the flow" refers to the flow cross-sectional area that is substantially perpendicular to the direction of the flow; and the term "the actual averaged velocity of fluid (or fluid flow)" refers to the averaged velocity of fluid in the direction of the flow. When an ultrasound transducer is used to image a region of interest in the body, ultrasound signals are sensed along scan lines in a plane known as the scan plane. The image is then displayed on a display screen to show a view of a section of the body within the region of interest on the scan plane and therefore corresponds to the scan plane. For this reason, the terms "scan plane" and "view" are used interchangeably in this application. As used herein, the phrase "locations substantially across the vessel" means locations that are spread out across one or more widths of the vessel so that an average of the velocity values taken at such locations yields a more accurate measure of the fluid flow mean velocity. The term "F-mode" indicates multi-range gate Doppler data acquisition and processing that provide at least velocity parameters from Doppler ultrasound echoes from moving objects (e.g. fluid flow), although energy and variance of velocity parameters may also be provided and processed as well if so desired. The term "F-mode data" means data acquired using such processing. An example of F-mode is the data acquisition and processing described in U.S. Pat. No. 5,014,710 to Samuel Maslak et al.

As shown below, the aspects of this invention may be used to obtain fluid flow information and cross-sectional area information of a vessel from not only Doppler shift information but also from time shifted information produced in a system such as that described in U.S. Pat. No. 4,928,698 and the article *"Time Domain Formulation of Pulse Doppler Ultrasound and Blood Velocity Estimation by Cross-Correlation,"* by Bonnefous et al., *Ultrasonic Imaging*, 8, 73–85 (1986).

One aspect of the invention is directed towards a method for measuring flow of a fluid in a vessel in the body, comprising the steps of producing a value of the velocity of the fluid from a Doppler or time shifted ultrasound signal from each of a plurality of locations on a first scan plane and located substantially across the vessel, and obtaining from said velocity values a first averaged velocity value and a first area measurement value. The method also comprises deriving values for the actual cross-sectional area of the flow and the actual averaged velocity of fluid from the averaged velocity value and area of measurement, and calculating from said actual cross-sectional area of the flow and the actual averaged velocity of the fluid a value of flow of the fluid in the vessel.

Another aspect of the invention is directed towards a method for measuring flow of a fluid in a vessel in a body using ultrasound equipment, comprising the steps of imaging a region of interest that includes an entire cross-section of the vessel by taking a first view of the image at a first angle to the vessel. The first set of velocity data and the first set of area measurement data are obtained for a first plurality of locations within the vessel as imaged in the first view. A second set of velocity data and a second set of area measurement data are obtained for a second plurality of locations within the vessel as imaged in the second view. The method further comprises deducing from said first and second sets of velocity data and from said first and second sets of area measurements a value of flow of the fluid in the vessel.

Another aspect of the invention is directed towards an apparatus for measuring flow of a fluid in a vessel in a body, comprising means for producing a value of the velocity of the fluid from a Doppler or time shifted ultrasound signal from each of a plurality of locations on a first scan plane and located substantially across the vessel, and means for obtaining from said velocity values an averaged velocity value and an area of measurement. The apparatus further comprises means for deriving values for the actual cross-sectional area of the flow and the actual averaged velocity of fluid from the averaged velocity value and area measurement, and means for deducing from said actual cross-sectional area of the flow and the actual averaged velocity of fluid the value of flow of the fluid in the vessel.

Yet another aspect of the invention is directed towards a method for measuring flow of the fluid in the vessel in a body, comprising the steps of obtaining blood flow parameters from a plurality of locations substantially across the vessel and in a plane, determining the average velocity of blood flow from said blood flow parameters; and determining a value of cross-sectional area of the vessel in said plane by integrating areas associated with information obtained from ultrasound echoes in the plane.

Still another aspect of the invention is directed towards a method for measuring cross-sectional area of a vessel in a body, comprising the steps of obtaining ultrasound echo information from a plurality of locations substantially across the vessel and in a plane, and determining a value of cross-sectional area of the vessel in said plane by integrating areas associated with said information.

The above-described system can also be used for measuring an averaged value of parameters of the fluid flow related to velocity, energy or variance of velocity information of a Doppler or time shifted signal from the fluid flow. Thus yet another aspect of the invention is directed towards a method for measuring flow of a fluid in a zone in a body, comprising the steps of designating a region of interest that encloses said zone, producing a value of a parameter related to velocity, energy or variance of velocity information of a Doppler or time shifted ultrasound signal from the flow at each of a plurality of locations in the region of interest in the body, and obtaining an averaged value of said parameter over said region.

BRIEF DESCRIPTION OF THE DRAWINGS

FIG. 1 is simplified ultrasound image of an artery where the scan plane intersects the artery along its length to illustrate a conventional method for measuring volumetric blood flow.

FIG. 2A is a schematic view of a section of a blood vessel and of a scan plane where the scan plane is oriented perpendicular to the surface of the body imaged for illustrating the invention.

FIG. 2B is a top view of the section of the blood vessel and scan plane of FIG. 2A together with the transducer generating ultrasound signals in the scan plane for illustrating the invention.

FIG. 2C is a side view of the section of the blood vessel and scan plane of FIG. 2A but where the scan plane is tilted to an inclined position (i.e. not perpendicular) relative to the surface of the body imaged for illustrating the invention.

FIGS. 2D–2H are schematic views of five different types of ultrasound transducers and their scan lines and scan planes for illustrating the invention.

FIG. 3 is a schematic view of a section of a blood vessel in a body and of a transducer for illustrating the preferred embodiment of the invention.

FIG. 4 is a view of the blood vessel of FIG. 3 from the surface looking into the body.

FIG. 5 is a view of a screen display showing displayed ultrasound images of the blood vessel of FIGS. 3 and 4 acquired using the transducer of FIG. 3.

FIG. 6 is a schematic view of the blood vessel and body of FIG. 3 where the transducer is tilted to different angles to obtain multiple measurements to illustrate the preferred embodiment of the invention.

FIG. 7 is a cross-sectional view of a blood vessel and pixels of a display covering the vessel to illustrate the invention.

FIGS. 8A, 8B together are a block diagram of an ultrasound system for measuring volumetric flow to illustrate the preferred embodiment of the invention.

FIG. 9 is a circuit diagram illustrating in more detail a portion of the circuit in FIG. 7B.

FIG. 10 a block diagram illustrating in more detail one implementation of the circuit of FIG. 9.

FIG. 11 illustrates another implementation and parallel to that of FIG. 10.

FIG. 12 is a schematic circuit diagram illustrating a circuit that may be useful for the implementation of FIG. 11.

FIG. 13 is a schematic representation of a lookup table for mapping inputs onto values for the purpose of counting qualified pixels, to illustrate the contents of the lookup tables in FIGS. 9–11.

FIG. 14 is a schematic representation of the implemented function of the lookup table of FIG. 13.

FIG. 15 is a schematic representation of a lookup table for mapping inputs onto values for the purpose of accumulating qualified velocity values, to illustrate the contents of the lookup tables in FIGS. 9–11.

FIG. 16 is a schematic representation of the implemented function of the lookup table of FIG. 15.

For convenience in description, identical components in the figures are labeled by the same numerals.

DETAILED DESCRIPTION OF THE PREFERRED EMBODIMENT

FIG. 2A is a schematic view of a portion of a blood vessel 2 within a body 20 with a surface 20a. The scan plane 22 intersects vessel 2 as shown. A Cartesian coordinate system XYZ is shown in FIG. 2 where the Z axis is perpendicular to the body surface 20a. The axis 10 of the vessel has a projection on surface 20a which is parallel to the X axis. In FIG. 2A, the transducer (not shown) that transmits ultrasound signals along scan lines in the scan plane 22 is oriented so that the scan plane 22 is normal to the body surface 20a and at an angle φ to the YZ plane shown more clearly in FIG. 2B. As described below in more detail, it is preferable to orient the scan plane so that it is in the YZ plane.

FIG. 2B is a top view of the section of the blood vessel 2 and scan plane 22 of FIG. 2A together with the transducer 30 generating ultrasound signals in the scan plane for illustrating the invention. As shown in FIG. 2B, the scan plane 22 is at an angle φ to the XZ plane and is normal to the body surface 20a. The preferred embodiment is described in reference to FIGS. 2A, 2B, 3–7. Before the preferred embodiment is described, it will be useful to consider the general case shown in FIG. 2C.

FIG. 2C is a side view of the section of the blood vessel and scan plane of FIG. 2A viewed along the Y axis but where the scan plane is tilted to an inclined position (i.e. not perpendicular) relative to the surface of the body imaged for illustrating the invention. In reference to FIG. 2C, the Z axis is normal to the surface of the body, and the angles in the figure are defined as:

$\theta_T$=the angle from the Z axis to the plane containing the scan plane of the transducer. This angle may be the result of tilting the transducer or steering the beams in an elevational direction or a combination of these;

$\theta_V$=the angle that the vessel makes with respect to the Z axis;

$\theta_{VT}$=the angle that the scan plane makes with respect to the vessel; and $\theta_{VT}=\theta_V-\theta_T$ The orientation of the blood vessel 2 with respect to the scanning plane is defined by two polar coordinate angles $\theta_{VT}$ and φ (defined above with respect FIG. 2B), as shown in FIG. 2C. Let $V_Y$ represent the component of the fluid flow velocity along the Y axis and $V_{XZ}$ the component of the fluid flow velocity in the XZ plane, as shown in FIG. 2C. Then if $\hat{x}, \hat{y}, \hat{z}$ are the unit vectors along the X, Y, Z axes respectively, then the actual velocity actual $V_{actual}$ of the fluid flow is given by:

$$v_{XZ} \sin \theta_V \hat{x} + v_Y \hat{y} + V_{XZ} \cos \theta_V \hat{z}$$

Because the Doppler effect can only measure the component of velocity radial to the scan (that is, the component in the scan plane), the measured velocity $V_{meas}$ at a point in space will be related to the actual velocity $V_{actual}$ at that time at a point in space through the following relationship:

$$V_{meas} = V_{XZ}\sin\theta_V(-\sin\phi\cos\phi_S\sin\theta_T + \cos\phi\sin\phi_S) +$$

$$V_Y(\cos\phi\cos\phi_S\sin\theta_T + \sin\phi\sin\phi_S) - V_{XZ}\cos\theta_V\cos\phi_S\cos\theta_T$$

where $V_{actual}$ can be obtained from $V_{XZ}$, $V_Y$. In the equation above, $\phi_S$ is the angle the ultrasound beam is steered in the non-elevation direction. FIGS. 2D–2H illustrate five different types of transducers that can be used to steer the ultrasound beam along either a constant or varying $\phi_S$. While transducers in these five types of steering formats can be used, it will be understood that formats other than these can also be used and are within the scope of this invention.

To measure volumetric flow it is also necessary to determine the actual area $A_{actual}$ which is perpendicular to the direction of the fluid flow. If ultrasound images are used to measure the actual area, the measured quantity $A_{meas}$ will need to be corrected according to the following relation:

$$A_{meas} = \frac{A_{actual}}{\left[\begin{array}{c}\sin^2\phi\cos^2\phi\sin^2\theta_T + \sin^4\phi\cos^2\theta_V\sin^2\theta_T + \\ \sin^2\phi\sin^2\theta_V\cos^2\theta_T - 2\sin^3\phi\sin\theta_V\cos\theta_V\sin\theta_T\cos\theta_T + \\ \cos^4\phi\cos^2\theta_V\sin^2\theta_T + \sin^2\phi\cos^2\phi\cos^4\theta_V\sin^2\theta_T + \\ \cos^2\phi\sin^2\theta_V\cos^2\theta_V\cos^2\theta_T - \\ 2\sin\phi\cos^2\phi\sin\theta_V\cos^3\theta_V\sin\theta_T\cos\theta_T\end{array}\right]^{1/2}}$$

If one uses the above equations for $V_{meas}$ and $A_{meas}$, to determine $V_{actual}$ and $A_{actual}$, one can determine the volume flow associated with each sample. One can then sum all of these flows to obtain a total volume flow.

The solutions to the above two equations for obtaining $A_{actual}$, $V_{actual}$ from $A_{meas}$, $V_{meas}$ can be simplified by assuming that the blood flow 6 within vessel 2 is substantially parallel to the vessel walls so that $V_Y$ is substantially zero, although the blood flow does not need to be at uniform velocities across any cross-section of the vessel.

If the scan plane is rotated so that the angle φ is substantially 90 degrees; and if a linear transducer format is used, then $\phi_S$ is zero. Then the above two equations reduce to:

$$V_{meas}=V_{actual}\times\cos\theta_{VT} \quad (1)$$

$$A_{meas}=A_{actual}/\sin\theta_{VT} \quad (2)$$

where $\theta_{VT}=\theta_V-\theta_T$

Of course, if a steered linear, vector, curved linear, sector or other transducer formats is used, it is possible to accommodate the dependence on $\phi_S$ by multiplying each sample processed by a known correction factor.

Data Acquisition

The above procedure in simplifying the two equations to obtain volumetric flow measurements will be illustrated in more detail in reference to FIGS. 3–7. In reference to FIG. 3, a transducer 30 is applied at a body/transducer interface 20a' with axis 26 of the transducer parallel to the Z axis and normal to surface 20a of the body. The transducer is rotated about its axis 26 until the gray-scale or B-mode image of a cross-section of vessel 2 has the smallest area. This is illustrated further in reference to FIGS. 4 and 5. FIG. 4 is a top view of vessel 2 looking from the surface 20a into the body 20. FIG. 5 is a schematic view of a displayed ultrasound image 40 obtained when an ultrasound system including transducer 30 is used to obtain the B-mode image of a cross-section of vessel 2. FIGS. 4 and 5 illustrate the views of the cross-sections of vessel 2 in three different positions A, B, C. Where the scan plane 22 intersects the vessel obliquely, such as at position C, the B-mode image appears on screen 40 as an elongated ellipse c. As the transducer is rotated so that the scan plane is in position B in FIG. 4, the cross-section of the vessel in image 40 is reduced from c to b. Where the cross-section of the vessel 2 has the smallest area, such as a, the scan plane is in position A in FIG. 4. When the transducer is in this position, the scan plane 22 would then be substantially perpendicular or normal to the X axis, and is in the YZ plane. Referring back to FIGS. 2A, 2B, when the scan plane is normal or perpendicular to the X axis so that it is in the YZ plane, the angle φ would be substantially 90 degrees, since the projection of axis 10 of the vessel on surface 20a is parallel to the X axis. Therefore, as long as the angle φ is maintained to be substantially 90 degrees during measurements, it is possible to remove the dependence of the measurements on the angle φ.

Instead of using B-mode image such as described above, the smallest cross-sectional area of the vessel can also be obtained by using F-mode data or other Doppler ultrasound data. Thus one may simply count and add the number of pixels on the screen where there is fluid flow indicated (e.g. count and add pixels where color is shown) as an indication of the cross-sectional area.

Dependence on the remaining angle θ0 may also be removed by a procedure described in reference to FIG. 6. FIG. 6 is the same side view of the vessel and transducer as that in FIG. 3, except that the transducer 30 has been rotated until φ is maintained to be substantially 90 degrees during measurements, and where the transducer has been tilted in the XZ plane to three different positions 30(1), 30(2), and 30(3) as shown in FIG. 6 in order to tilt the scan planes to three different angles $\theta_1$, $\theta_2$ and $\theta_3$. As noted below, the tilting of the scan planes can also be accomplished by beam steering without actually moving the transducer.

Before describing how the angular dependence on θ can be removed, it will first be useful to examine the angular dependence of the measured area and velocity on θ. Volumetric flow Q is normally measured in units of milliliters per second. The instantaneous volumetric flow Q(t) is a function of time, and is given as the integral of the surface integral of the instantaneous velocity v(x,y,t) at position (x,y):

$$Q(t) = \int_A \int_{(t)} v(x,y,t)\, dx\, dy$$

over the instantaneous cross-sectional area A(t) of the vessel. The time-averaged volumetric flow of Q is:

$$\overline{Q} = \frac{1}{T} \int_0^T Q(t)\, dt = \frac{1}{T} \int_0^T \int \int_{A(t)} v(x,y,t)\, dx\, dy\, dt$$

The selected time interval is typically one or more integral cardiac or heart cycles, or might be only during a certain interval within the cardiac cycle. If the velocity is a constant V over time and over the flow surface intersected by the scan plane, and the surface is a constant area A, then:

$$\overline{Q} = \frac{1}{T} \int_0^T \int_x \int_y v(x,y,t)\, dx\, dy\, dt =$$

$$\frac{V}{T} \int_0^T \int_x \int_y dx\, dy\, dt = \left(\frac{V}{T}\right)(TA) = VA$$

This product relation will be used to estimate volumetric flow as shown below.

After the angle φ has been set to substantially 90 degrees in the procedure described above in reference to FIGS. 3–5, transducer 30 is tilted in the XZ plane to different positions where $\theta_{VT}$ having the value 0°, 90°, 180° or 270° is avoided since either the velocity or area is not measurable at these angles. Where transducer 30 is tilted in the XZ plane to positions 30(1)–30(3), velocity and area measurements can be taken with the transducer in these positions. Preferably the transducer is tilted or the scan line steered in the elevational direction so that $\theta_{VT}$ is in the range of about 15 to 75 degrees, or more specifically about 30 to 60 degrees. The exact angle need not be known; however, angles closer to 45° plus integer multiples of 90° are better than angles that deviate from this by a large number of degrees.

Consider the rectangular raster grids 36 of pixels that represent the F-mode data in FIG. 7, which is a cross-sectional view of vessel 2 on screen 40 where the color Doppler is "lit up" with a color only in pixels which are shaded. In other words, either because of blockage or other reasons, there may not be blood flow through the entire cross-section of the blood vessel but only through some portions of the cross-section. In such event, it may be desirable to calculate volumetric flow based on only the portions of the cross-section where there is qualified blood flow data but ignore portions or pixels in the cross-section where blood flow is not present.

For a given display setting, $A_{pix}$ represents the constant area associated with each pixel. The imaging frames are designated by index m, and each frame separated from the next frame by Δt seconds. Rather than calculating the instantaneous volumetric flow associated with each frame, one may simply determine for each frame or for a number of frames the average velocity V and the average area A which have been corrected for the angular dependence on θ. Then the averaged volumetric flow is simply given by the product VA. The constant Apix is computed based upon the display settings. Assuming that the time-averaging interval (0, T) is covered by M frames for m ranging from 0 to M−1, then the following equations may be used to eliminate the explicit dependence of the measurement on θ in the two simplified equations (1) and (2) above. If the index k (ranging from 1 to K) is used to designate the averaged measurements for $A_k$ and $V_k$ at an angle $\theta_k$, so that the approximations below will hold:

$$A_k = (1/M) \sum_m \sum_i \sum_j p_k(m,i,j) \Delta x \Delta y$$

where $p_k(m,i,j)$ is one if the pixel is color activated and 0 if the pixel is not activated, which means that the following holds:

$$A_k = \frac{A_{pix}}{M} \sum_m \sum_i \sum_j p_k(m,i,j)$$

and $$V_k = \frac{\sum_m \sum_i \sum_j V_k(m,i,j) \cdot p_k(m,i,j)}{\sum_m \sum_i \sum_j p_k(m,i,j)}$$

Ideally, $$A = A_{actual} = A_k \sin\theta_k$$

$$V = V_{actual} = \frac{V_k}{\cos\theta_k}$$

but noise and approximation makes these equations inaccurate. Again ideally, $$\left(\frac{A}{A_k}\right)^2 + \left(\frac{V_k}{V}\right)^2 = \sin^2\theta_k + \cos^2\theta_k = 1$$

Deviations from ideal can be used to form the error:

$$e_k = \left(\frac{A}{A_k}\right)^2 + \left(\frac{V_k}{V}\right)^2 - 1$$

Forming the total squared error E or f (A, V) over a number of angles:

$$E = \sum_{k=1}^{K} e_k^2 = \sum_{k=1}^{K} \left[ \left( \frac{A}{A_k} \right)^2 + \left( \frac{V_k}{V} \right)^2 - 1 \right]^2$$

The squared error can be minimized using a least mean square error estimate calculation so that the averaged area A and averaged velocity V will not explicitly depend on angle $\theta_k$.

The calculations for determining the values for A and V that will minimize the least mean square error E are set forth in Appendix A attached hereto and made part of this application. As shown in the Appendix A, N measurements are taken ranging from 0 to N–1, where each measurement results in a time and area averaged measurement of velocity $V_i$ and a time averaged value $A_i$ for cross-sectional area where i ranges from 0 to N–1. The values of A, V that will minimize E are then obtained. The volumetric flow is then given by the product AV.

If N is 2, then the exact solution and the least mean square error calculation are the same. While preferably, the angular dependence on $\theta$ can be eliminated as described above, in some applications, it may be adequate to perform a direct measurement of the angle $\theta$ as described above in reference to FIG. 1. In such event, all one has to do is to orient the transducer 30 so as to eliminate the dependence upon the angle $\phi$ such as by the procedure described above in reference to FIGS. 3–6, and the actual cross-sectional area and the actual average velocity may then be obtained by multiplying the result obtained in one measurement by appropriate factors using knowledge of $\theta$. Such and other variations are within the scope of the invention.

In the description above, transducer 30 is of the type where the scan lines are in the azimuth plane of the transducer so that it is generally not possible to change direction of the scan line in the elevational direction of the transducer. Where it is possible to steer the scan line both in the azimuth and elevation directions, rotation and tilting of the transducer may not be required so that the rotation and the tilting of the scan plane described above may be accomplished by applying appropriate signals with the proper phase relationship in a manner known to those skilled in the art.

While the invention has been described above by rotating and tilting the transducer 30 with the contacting surfaces between the transducer and the body 20 remaining unchanged, it will be understood that essentially the same results as those described above can be obtained even where the same contact point is not maintained in the rotational and tilting process as long as the general orientation of the transducer relative to the body and the vessel remain the same as that described above. Such and other variations are within the scope of the invention. In this connection, the term "skin/transducer interface position" means that the contact point between the transducer and the surface of the body 20a does not change when the transducer is rotated or tilted (or tipped) to make measurements at the different imaging angles.

The term "rotationally orienting" as used herein means rotating the transducer while its axis is perpendicular or normal to the surface of the body. The term "tilted angle" means the angle that the axis of the transducer makes with the normal direction to the surface of the body.

Processing of the Acquired Data

FIGS. 8A, 8B together are a block diagram of an ultrasound system to illustrate the preferred embodiment of the invention. As shown in these two figures, system 100 includes transducer 30 connected to an ultrasound beamformer 102 that applies appropriate signals to the transducer for transmitting ultrasound signals towards a body that includes a vessel containing moving fluid such as blood (not shown). The ultrasound signals are transmitted sequentially along scan lines (not shown) spanning a scan plane in a region of interest. The echoes of the ultrasound signals reflected off of the body including the moving fluid and vessel are detected by the transducer 30 whose output is applied to the beamformer 102. The output of the beamformer is processed by a B-mode processing unit 104 to provide a gray-scale, B-mode image. The output of the beamformer is also applied to a F-mode processing unit 106 in which the received signal is processed to extract velocity information which is stored in CINE memory 108 which also stores the B-mode image from the B-mode processing unit. Either one or both of the B-mode and F-mode images may be retrieved and scan converted by scan conversion 110 and applied to two frame buffers 112, 114: Image plane 0 and image plane 1. The reading and writing of image information into or out of memory 108 is controlled by microprocessor 120 employing a write address unit 122 and a read address unit 124. Each of the two frame buffers 112, 114 may be divided into sections, each for storing data of an image type, such as B-mode, color-energy, color-variance, color-velocity data.

Both buffers 112, 114 include a section for storing the identity of pixels within the region designated by a user, or the region ID. The user may designate the region or regions where the volumetric flow is to be calculated, referred to herein as calculation area, by means of a trackball input 130. As known to those skilled in the art, the user may simply draw an outline of the regions where volumetric flow is of interest on a display device. Such input will be processed by microprocessor 120 and recorded in the region ID section of the frame buffers. In some applications, the outline drawn by the user is actually shown on the display screen. The use of two frame buffers facilitates the display process. While the scan converted data is written into one buffer, the data already written into the other buffer may be retrieved through a multiplexer 132 as controlled by the microprocessor so that the different image types of data as well as region ID data for the same pixel may be retrieved at the same time for display by device 140 in FIG. 8B. It is possible also for an operator to set up the system so that the area of the vessel is the only area in the displayed image for which F-mode data is displayed. Then there is no need for the operator to designate a calculation area using the trackball, and the entire F-mode area displayed is the calculation area.

The output of multiplexer 132 includes the different image type data and/or region Id. In signal path 138, image data is applied to display device 140 for displaying B-mode and F-mode images in a manner known to those skilled in the art. The image data is also applied along signal path 136 to parameter selection 142 and the region Id information is applied to calculation area accumulators 144. Parameter selection 142 in response to the microprocessor selects the appropriate bits of information from the B-mode and F-mode information and supplies such bits to the lookup table 146. Lookup table 146 maps such bits onto values that are supplied to accumulators 144. Instead of lookup tables 146, other mapping devices such as threshold or scaling devices may also be used.

In operation of the system of FIGS. 8A, 8B, the operator displays the B-mode image and traces out one to N calculation areas within which volume flow measurements are to be made. The area enclosed by each of the uniquely enclosed calculation area of interest outlines is given a unique identifier which is placed into the region Id bit locations of the image memory planes 112, 114 corresponding to the enclosed area as shown on the display device.

FIG. 9 is a schematic circuit diagram illustrating in more detail the functions and construction of parameter selection 142, accumulators 144 and lookup table 146. As shown in FIG. 9, parameter selection 142 includes two parameter select logic circuits 142a, 142b for selecting the appropriate B-mode and F-mode information to determine the actual area where there is fluid flow, and flow velocity.

The bits selected by logic 142a are supplied to lookup table 146a which applies a selection criteria to such bits to determine whether there is valid fluid flow data in the particular pixel for displaying the data. If there is, table 146a would output 1 to AND-gate 150. Otherwise, it will supply a 0 to the AND-gate. The region Id enable bit of line 136 is also supplied to AND-gate 150, so that if the particular pixel data processed is not within the calculation area designated by the user, a 0 is supplied to AND-gate 150 to force the gate output to 0 so that such pixel is not counted in the accumulator 144a; otherwise a 1 is supplied to gate 150. If AND-gate 150 supplies a 1 to adder 152, adder 152 adds this value to the value stored in the accumulator register 144a and applies this updated value to replace the one stored in the register 144a. In this manner, the B-mode information and/or F-mode information may be used to determine whether there is flow in the particular pixel and whether the pixel should be counted as part of the actual area where there is fluid flow. For example, if the amplitude of the B-mode signal is high, this may indicate that the color present in such pixel may not be a reliable indication of fluid flow in such pixel so that the lookup table 146a should output a 0 rather than a 1. In some applications, just the F-mode data may be adequate for determining the validity of the data. The same considerations also apply to qualifying the validity of the velocity data processed in the parallel path described below.

Parameter select logic 142b would select the appropriate bits of information from the F-mode and B-mode information from multiplexer 132 and supply such bits to the lookup table 146b. In a manner similar to that described above for lookup table 146a, table 146b applies a selection criteria to the bits received to output a value for velocity if the data is qualified and a 0 if the data is not qualified as valid to AND-gate 154, which may be a multi-bit gate. AND-gate 154 is also controlled by the region Id enable bit from the multiplexer 132 in a manner similar to AND-gate 150. Adder 156 then adds the output of AND-gate 154 to the stored value in register 144b and supplies the updated value to replace that stored in accumulator register 144b.

Frame buffers 112 and 114 each stores an entire frame of information. After an entire frame of information has been processed through the two signal paths in FIG. 9, accumulator 144a will contain a count indicating the number of qualified pixels in the vessel where there is significant fluid flow and accumulator 144b will contain a summed value of a parameter such as velocity. The values stored in the two registers 144a, 144b are then read by the microprocessor through two tri-state buffers 158 controlled by the microprocessor and stored in the microprocessor memory.

The above-described process for counting the number of qualified pixels where there is actual flow and integration to obtain a sum of qualified velocity values may be performed for each of multiple frames. By multiplying the number of pixels by the area per pixel an area measurement is obtained for each of the multiple frames. By dividing the sum of qualified velocity values by the number of qualified pixels, an averaged velocity for each of the several frames is obtained. Processing and display of the result may occur immediately after real-time acquisition has occurred or it may occur at a later point in time as the data is read out of the cine memory. While in the preferred embodiment, the cross-sectional area is given by counting qualified pixels and multiplying the count by the pixel area, it will be understood that other methods of integrating qualified area portions may be used and are within the scope of the invention.

One possible processing sequence for acquired frames might be:

```
REPEAT FOR (selected set of acquisition angles) {
    FOR EACH DISPLAYED FRAME {
        Processor waits for the start of vertical blank (Fig.8A)
        Processor acquires from the hardware for the previously displayed frame
            FOR EACH REGION_ID {
                read from the hardware the total number of pixels displaying qualified color as
                    calculated by the hardware
                    read from the hardware the sum of all qualified velocity values at pixels in a given region
            }
            processor clears accumulators
    }
}
```

After a designated number of frames have been processed, microprocessor 120 then computes an averaged area measurement and an averaged velocity for the multiple frames. These then are the measured area and averaged velocity values for a particular angle of measurement θ between the scan plane and the fluid flow in the vessel. Once the processor has all the data required to perform a given calculation, it may perform the calculation and display the result. The display may be in the form of either a numeric value or a waveform display. The actual order of displaying frames also does not need to correspond to the order in which the frames were acquired. To display a numeric value, microprocessor 120 provides the value via line 160 to the text and graphics plane 162. For waveforms the data is also sent to the text and graphics plane.

As indicated above, the angle θ may actually be measured so that the values stored in the two registers may be corrected using the information obtained and measured to yield the actual area and velocity and therefore the volumetric flow. Alternatively, the values may be stored in a microprocessor memory as the area measurement value and averaged velocity for a particular scanning and measuring position such as one of the three illustrated in FIG. 6. The transducer may then be tilted to a different angle as described above in reference to FIG. 6 and the above data acquisition process repeated to obtain another measured value of the averaged area and averaged velocity to be stored at the microprocessor memory. This process may be repeated if desired to obtain multiple values of the measured area and velocity. The microprocessor then performs the least mean square error estimate calculations described above to obtain the values of area and velocity that will minimize the mean square error. The product of these two quantities then yields a volumetric flow in vessel 2. Alternatively, the data acquired at each angle may be stored in cine memory and the processing can occur later.

In the description above, the velocity data is used to determine whether there is qualified blood flow in a certain pixel or area, so as to decide whether such pixel or area is to be counted or added to arrive at the total cross-sectional area of the vessel. It is possible to use data other than velocity of the blood flow in this process. For example, non-zero energy or variance of velocity of the flow within the calculation area may be used instead. Other types of data may also be used, such as B-mode data, or other ultrasound echo information. An estimate of the cross-sectional area of the vessel is then obtained by adding or integrating areas associated with such information. All such variations are within the scope of the invention.

Averaging Over Cardiac Cycle or Portion Thereof

During the acquisition step, the acoustic data associated with each frame of data to be processed along with the respective time stamp (i.e., the time at which the frame was acquired) as well as the time at which various reference signals occurred (e.g., the Rwave trigger in a cardiac cycle) are acquired and saved. Physio unit 103 in FIG. 8A acquires electrocardiograms from which Rwave trigger signals are derived. These trigger signals together with the acoustic data may be passed to the display directly or may be passed at a later time via a cine operation.

The display subsystem consists of scan converting the acoustic data and placing it into a specified image memory plane; once the entire image has been scan-converted, one will at a later vertical blank signal read the scan-converted signal from the image memory and process the scan-converted data on its way to the display device.

In the data acquisition process described above, consecutive frames of acoustic data spanning several Rwave cycles may be obtained. Along with the acoustic data, the time stamps associated with the acquired frames as well as the time stamps for any reference signals are also stored.

A couple of examples are:

sums by 24) of the velocity and pixel counts for each of the three angles scanned to obtain three sets of averaged values. A least mean square error calculation is then performed to find an area value and a velocity value that would minimize the error for the data acquired at the three angles. These values would then be used to calculate volume flow.

An alternative approach might be for the processor to average for each angle the three values obtained at the same relative offset with respect to the start of the Rwave (i.e., sum over all j, for particular value(s) of k). This results in a separate value of summed velocity and pixel count to calculate an instantaneous volume flow. This means that the averaging is performed over a group of frames having the same time offset relative to a cardiac event such as an Rwave trigger. For example the averaging may be performed for frames $F(1,1,2)$, $F(1,2,2)$ and $F(1,3,2)$ to obtain an averaged area measurement and averaged velocity for the second frame in the cardiac cycle for unique scan angle 1. The averaging is then performed for frames $F(2,1,2)$, $F(2,2,2)$ and $F(2,3,2)$ to obtain an averaged area measurement and averaged velocity for the second frame in the cardiac cycle for unique scan angle 2; and for frames $F(3,1,2)$, $F(3,2,2)$ and $F(3,3,2)$ to obtain an averaged area measurement and averaged velocity for the second frame in the cardiac cycle for unique scan angle 3. Then a least mean square error estimate calculation is performed on the three sets of averaged area measurements and averaged velocities to obtain the averaged area and velocity that cause the squared error to be minimum. In this example, each of the three groups of frames includes three frames, and each of the frames is the second frame (k has the value 2) after the Rwave trigger. Obviously, each group may include more than three frames (e.g. k=2,3 where each group has six frames); all such variations are within the scope of the invention.

In the case where the data averaged only over frames spanning a portion of the cardiac cycle, if one were using a cine memory, the frames need not be displayed in order but might instead be displayed in an order corresponding to the lowest offset with respect to the start or trigger of the Rwave.

In addition, one could gather the accumulated count and velocity information for each display region all within the same display refresh or raster scan interval or in order to reduce the hardware, one might display the same data for multiple display intervals and acquire only a subset of the entire set of values during any one display refresh interval. One may also display the acquired data for all frames, and then mix and match the results from various frames without having to re-display the frames.

---

Let $F(i,j,k)$ represent the kth acoustic frame acquired relative to the jth Rwave trigger for the ith unique angle of scan. One might then have acquired the following frames of data:

$F(1,1,1),F(1,1,2),F(1,1,3),F(1,1,4),F(1,1,5),F(1,1,6),F(1,1,7),F(1,1,8)$
$F(1,2,1),F(1,2,2),F(1,2,3),F(1,2,4),F(1,2,5),F(1,2,6),F(1,2,7),F(1,2,8)$
$F(1,3,1),F(1,3,2),F(1,3,3),F(1,3,4),F(1,3,5),F(1,3,6),F(1,3,7),F(1,3,8)$
$F(2,1,1),F(2,1,2),F(2,1,3),F(2,1,4),F(2,1,5),F(2,1,6),F(2,1,7),F(2,1,8)$
$F(2,2,1),F(2,2,2),F(2,2,3),F(2,2,4),F(2,2,5),F(2,2,6),F(2,2,7),F(2,2,8)$
$F(2,3,1),F(2,3,2),F(2,3,3),F(2,3,4),F(2,3,5),F(2,3,6),F(2,3,7),F(2,3,8)$
$F(3,1,1),F(3,1,2),F(3,1,3),F(3,1,4),F(3,1,5),F(3,1,6),F(3,1,7),F(3,1,8)$
$F(3,2,1),F(3,2,2),F(3,2,3),F(3,2,4),F(3,2,5),F(3,2,6),F(3,2,7),F(3,2,8)$
$F(3,3,1),F(3,3,2),F(3,3,3),F(3,3,4),F(3,3,5),F(3,3,6),F(3,3,7),F(3,3,8)$

---

The above frames might be displayed in the same manner as that described above. The processor may then obtain averages from the 24 resulting values (i.e., sum over all j and k for each of the three frames 1, 2, 3, and divide each of the While the invention has been described above by reference to an implementation where the parameter selection, mapping using the lookup table and accumulation are performed digitally by operating on scan converted data, it will be evident that this is not required and these processes can be performed before the scan conversion. The process to adapt the above described procedure for performance prior to scan conversion would be especially simple for data acquired with linear transducer formats.

While the above apparatus has been described for performing an averaging function on area and velocity, it will be understood that a similar process can also be applied to other ultrasound parameters such as energy or variance of velocity, with or without performing an averaging function on area as well. In some applications it may also be useful to measure just the cross-sectional area of the fluid flow in the manner described without also measuring other flow parameters. All such variations are within the scope of the invention. In the preferred embodiment described above, all of the qualified pixels in the vessel are counted to arrive at a cross-sectional area, and all the qualified velocities values are summed to arrive at the averaged velocity. In some applications, it may be adequate to count a smaller number of such pixels, and sum the qualified velocities also at a smaller number of these pixels, if the distribution of velocities of the flow at the counted pixels and pixels where velocities are summed is representative of the fluid flow. For example, it may be adequate to take into account only the pixels distributed across one or more widths of the vessel. All such variations are within the scope of the invention.

One implementation of the embodiment of FIG. 9 is illustrated in more detail in the block diagram of FIG. 10, which includes circuit functions equivalent to the image planes of FIG. 8A and the circuit 200 which performs all the functions of FIG. 9. As shown in FIG. 10, the parameter selection, lookup table and pixel accumulator circuit 200 receives F-mode and B-mode data from three image planes 212, 214 and 216 which are respectively the Image Type 0, Image Type 1 and Image Type 2 planes in buffers 112, 114 of FIG. 8A. Data from the three planes are supplied in parallel to two multiplexers 242a and 242b controlled by two select lines A select, B select from register 202. Each of the two multiplexers selects the appropriate bits of information from such inputs and supplies such information to a corresponding random access memory lookup table 246a or 246b. The two lookup tables are controlled by page selects $PAGE_A$, $PAGE_B$ from register 202.

Circuit 200 includes two pairs of accumulators: a first pair 244a(1), 244a(2) and a second pair 244b(1), 244b(2). In each pair, one is for accumulating or integrating even-numbered pixels and the other for integrating or accumulating odd-numbered pixels. The two accumulators in each pair for accumulating even and odd pixels are arranged in parallel to speed up the accumulation process.

The two lookup tables map the received bits onto selected stored values under the control of the two page signals and supply outputs to the accumulators through two sign extension controls 248, with each of the controls supplying sign extended signals to a pair of two accumulators. Each of the four accumulators has sixteen registers addressed by a four bit region address signal from pixel control map 218 which performs a function similar to the region Id section of the image planes of FIG. 8A. In this manner, each of the four accumulators is capable of accumulating up to sixteen different calculation areas. Pixel control map 218 sends an extra two bits for A enable and B enable control, which permits all four accumulators to be used for accumulating a single parameter such as area or velocity, without accumulating the values of a second parameter. The implementation of the circuitry of FIG. 10 is illustrated in more detail in a microfiche appendix entitled "Ultrasound System for Flow Measurements Implementation No. 1," which is attached hereto and is an integral part of this application.

FIG. 11 illustrates another implementation parallel to that of FIG. 10; the implementation in FIG. 11 is illustrated in more detail in microfiche appendix entitled "Ultrasound System for Flow Measurements Implementation No. 2," which is attached hereto and is an integral part of this application. As shown in FIG. 11, system 300 has essentially the same overall structure as that in FIG. 10 except that the number of multiplexers (e.g. 342), random access memory lookup tables (e.g. 346) and accumulators (e.g. 344(1), 344(2)) have been reduced for a more cost-effective implementation. For this reason, additional control circuits such as control register file 302, A/B select register 304, and multiplexers 306, 308 are used for controlling parameter select multiplexer 342, random access memory lookup table 346, sign extension control 348, and accumulators 344 (1), 344 (2).

FIG. 12 is a schematic circuit diagram illustrating a circuit 350 that may be useful for the implementation of FIG. 11. Since it takes considerable time to read a value from each of the two accumulators 344(1), 344(2), when such value is read and sent to adder 352 as in FIG. 11, such value may already be stale and should be replaced by a more updated value instead. The circuit of FIG. 12 compensates for this by using the circuit 350 where a region Id collision detector 351 compares the region Id that is associated with the value at the input to the accumulator with the region Id associated with the value being written to memory 344', and selects which of the multiplexer 360 inputs to be applied to adder 352'.

FIG. 13 is a schematic representation of a lookup table for mapping input values onto values for the purpose of counting qualified pixels, to illustrate the contents of the lookup tables 146a, 246a and a corresponding portion of 346 described above in reference to FIGS. 9–11. As shown in FIG. 13, both velocity and B-mode values are sent to the lookup table which maps the velocity and B-mode values to a value which is supplied to its output. FIG. 14 is a schematic representation of the implemented function of the lookup table of FIG. 13. As shown in FIG. 14, the lookup table would output a "1" when the B-mode intensity is below a predetermined threshold 402 and if the velocity is above a threshold 404 in one direction or above a threshold 406 in the other direction. Otherwise, the lookup table would supply a zero at its output.

FIG. 15 is a schematic representation of a lookup table for mapping inputs onto values for the purpose of accumulating qualified velocity values, to illustrate the contents of the lookup tables 146b, 246b and a corresponding portion of table 346 described above in reference to FIGS. 9–11. As shown in FIG. 15, both velocity and B-mode values are sent to the lookup table which maps the velocity and B-mode values to a value which is supplied to its output. FIG. 16 is a schematic representation of the implemented function of the lookup table of FIG. 15. As shown in FIG. 16, the lookup table would output a baseline corrected velocity value when the B-mode intensity is below a predetermined threshold 412 and if the velocity is above a threshold 414 in one direction or above a threshold 416 in the other direction. Otherwise, the lookup table would supply a zero at its output. The process for loading the lookup tables in FIGS. 13, 15 so that their implemented functions will be as shown in FIGS. 14, 16 is set forth in APPENDIX B, which is attached hereto and forms an integral part of this application.

The invention has been described up to this point by operations on Doppler information signals containing Doppler information. Essentially the same advantages can be obtained if the same scheme is employed to obtain parameters related to velocity (as well as energy and variance of velocity parameters) and cross-sectional area of the flow from time shifted information instead of Doppler information. U.S. Pat. No. 4,928,698 describes a system employing time shifted information for deriving parameters related to blood flows and motion of organs. The circuits and generalized schemes described above may be used to obtain the parameters from time shifted information in a system such as that described in U.S. Pat. No. 4,928,698 and the article "Time Domain Formulation of Pulse Doppler Ultrasound and Blood Velocity Estimation by Cross-Correlation," by Bonnefous et al., *Ultrasonic Imaging*, 8, 73–85 (1986).

While the invention has been described above by reference to various embodiments, it will be understood that different changes and modifications can be made without departing from the scope of the invention which is to be limited only by the appended claims.

APPENDIX A $A = A_t \sin \theta$ $V = V_f \cos \theta$ $A$ = true cross-sectional area
$V$ = true time and area averaged velocity surface integral
$A_i$ = the time averaged measurement of cross-sectional area at angle $\theta$
$V_i$ = the time and area averaged measurement of velocity surface integral at the angle $\theta$ $\sin \theta = A/A_i$ $\cos \theta = V_i/V$ The equations below are used to determine the value of $A$ and $V$ that will minimize the Least Mean Square Error where $N$(0 to $N-1$) measurements are taken, so that $i$ ranges from 0 to $N-1$ for $A_i$, $V_i$.

$$f(A, V) = \sum_{i=0}^{N-1} \left( \left( \frac{A}{A_i} \right)^2 + \left( \frac{V_i}{V} \right)^2 - 1 \right)^2$$

$$\frac{\partial f}{\partial A} = 2 \sum_{i=0}^{N-1} \left( \left( \frac{A}{A_i} \right)^2 + \left( \frac{V_i}{V} \right)^2 - 1 \right) \left( \frac{2A}{A_i^2} \right) = 0 \quad (1)$$

$$\frac{\partial f}{\partial V} = 2 \sum_{i=0}^{N-1} \left( \left( \frac{A}{A_i} \right)^2 + \left( \frac{V_i}{V} \right)^2 - 1 \right) \left( \frac{-2V_i^2}{V^3} \right) = 0 \quad (2)$$

Simplifying the equations for $$\frac{\partial f}{\partial A} = 0 \text{ and } \frac{\partial f}{\partial V} = 0$$

we obtain $$4A \left[ \sum_{i=0}^{N-1} \frac{A^2}{A_i^4} + \sum_{i=0}^{N-1} \left( \frac{V_i}{A_i} \right)^2 \left( \frac{1}{V^2} \right) - \sum_{i=0}^{N-1} \left( \frac{1}{A_i} \right)^2 \right] = 0 \quad (3)$$

from (1) and $$\frac{-4}{V^3} \left[ \sum_{i=0}^{N-1} A^2 \left( \frac{V_i}{A_i} \right)^2 + \sum_{i=0}^{n-1} \frac{V_i^4}{V^2} - \sum_{i=0}^{N-1} V_i^2 \right] = 0 \quad (4)$$

from (2)

further simplification of (3) and (4) yields:

$$A^2 \sum_{i=0}^{N-1} \left( \frac{1}{A_i} \right)^4 + \frac{1}{V^2} \sum_{i=0}^{n-1} \left( \frac{V_i}{A_i} \right)^2 - \sum_{i=0}^{N-1} \left( \frac{1}{A_i} \right)^2 = 0 \quad (5)$$

$$A^2 \sum_{i=0}^{N-1} \left( \frac{V_i}{A_i} \right)^2 + \frac{1}{V^2} \sum_{i=0}^{n-1} V_i^4 - \sum_{i=0}^{N-1} V_i^2 = 0 \quad (6)$$

This can be expressed in matrix form as $$\begin{bmatrix} m_{11} & m_{12} \\ m_{21} & m_{22} \end{bmatrix} \begin{bmatrix} X_1 \\ X_2 \end{bmatrix} = \begin{bmatrix} R_1 \\ R_2 \end{bmatrix}$$

where $$m_{11} = \sum_{i=0}^{N-1} \left( \frac{1}{A_i} \right)^4 \quad m_{12} = \sum_{i=0}^{N-1} \left( \frac{V_i}{A_i} \right)^2$$

$$R_1 = \sum_{i=0}^{N-1} \left( \frac{1}{A_i} \right)^2$$

$$m_{21} = \sum_{i=0}^{N-1} \left( \frac{V_i}{A_i} \right)^2 \quad m_{22} = \sum_{i=0}^{N-1} V_i^4 \quad R_2 = \sum_{i=0}^{N-1} V_i^2$$

$$X_1 = A^2 \quad X_2 = \frac{1}{V^2}$$

$$X_1 = \frac{R_1 m_{22} - R_2 m_{12}}{m_{11} \cdot m_{22} - m_{12} \cdot m_{21}}$$

$$X_2 = \frac{R_2 m_{11} - R_1 m_{21}}{m_{11} \cdot m_{22} - m_{12} \cdot m_{21}}$$

$$\therefore A = \sqrt{\frac{R_1 m_{22} - R_2 m_{12}}{m_{11} \cdot m_{22} - m_{12} \cdot m_{21}}}$$

$$V = \sqrt{\frac{m_{11} \cdot m_{22} - m_{12} \cdot m_{21}}{R_2 m_{11} - R_1 m_{21}}}$$

$$F = AV = \sqrt{\frac{R_1 m_{22} - R_2 m_{12}}{R_2 m_{11} - R_1 m_{21}}} =$$

$$\sqrt{\frac{\left( \sum_{i=0}^{N-1} \left( \frac{1}{A_i} \right)^2 \right) \left( \sum_{i=0}^{N-1} V_i^4 \right) - \left( \sum_{i=0}^{N-1} V_i^2 \right) \left( \sum_{i=0}^{N-1} \left( \frac{V_i}{A_i} \right)^2 \right)}{\left( \sum_{i=0}^{N-1} V_i^2 \right) \left( \sum_{i=0}^{N-1} \frac{1}{A_i^4} \right) - \left( \sum_{i=0}^{N-1} \frac{1}{A_i^2} \right) \left( \sum_{i=0}^{N-1} \left( \frac{V_i}{A_i} \right)^2 \right)}}$$

APPENDIX B

LoadVolumeFlowFunctionA (velThresh, B-modeThresh, mapptr)

velThresh is the velocity threshold. If the absolute value of the velocity input (treated as an 8-bit signed number) into the hardware lut is below this threshold, then the output of the lut will be set to 0. If the b-mode input is above the BmodeThreshold level, then the output will also be set to 0. Otherwise the output will be set to a 1. This function mimics the thresholding functions performed in the color mapping.

The mapptr is a pointer to the hardware lut RAM page that will be loaded with function A.

The LUT is organized as shown in FIGS. 13 and 14:

```
*       Author: Ismayil Guracar
*       Date: 4/26/95
*       Copyright: Acuson
*/
Load    VolumeFlowFunctionA(velThresh, BmodeThresh, mapptr)
int     velThresh;
int     BmodeThresh;
int     *mapptr;
{
int     vel, b, flag;
for     (vel=0; vel<256; vel++)
  {
    if (vel<128)
        if (vel<velThresh)
            flag=0;  /* color is off */
        else
            flag=1;  /* color is on */
    else /* vel negative */
        if ((255-vel)<velThresh)  /* absolute value of velocity */
            flag=0;  /* color is off */
        else
            flag=1;  /* color in on */
    for (b=0; b<BmodeThresh; b++)
        mapptr[(vel<<8)+b] = flag;
    for (b=BmodeThresh; b<256; b++)
        mapptr[(vel<<8)+b] = 0;  /* set color off */
  }
}
*
*
*   LoadVolumeFlowFunctionB(velThresh, BmodeThresh, BaselineShift, mapptr)
*
*       velThresh is the velocity threshold. If the absolute value of the
*       velocity input (treated as an 8-bit signed number)
*       into the hardware lut is below this threshold, then the
*       output of the lut will be set to 0. If the b-mode input
*       is above the BmodeThreshold level, then the output will also
*       be set to 0. Otherwise the output will be set to the baseline
*       shift corrected velocity input.
*
*       The BaselineShift value operates as follows:
*
*
*       positive values:
*
*       In      0   ...  v   ...   127+Baseline Shift
*       Out     0   ...  v/2 ...   127baseline Shift/2
*
*
*       negative values:
*
*       In      255 ...  v   ...   128-BaselineShift
*       Out (-1) ... -(256-v)/2 ... ((-128) +BaselineShift)/2
```

```
*       Copyright: Acuson
*/
iead    VolumeFlowFunctionB(velThresh, BmodeThresh, BaselineShift, mapptr)
int     velThresh;
int     BmodeThresh;
int     *mapptr;
int     vel, b, flag;
int     baselineCorrectedVelocity;
for     (vel=0; vel<256; vel++)
/
*
*       implement velocity threshold
*/
    if (vel<128)
        if (vel<velThresh)
            flag=0;  /* color is off */
        else
            flag=1;  /* color is on */
    else /* vel negative */
        if ((255-vel)<velThresh)  /* absolute value of velocity */
            flag=0;  /* color is off */
        else
            flag=1;  /* color in on */
```

```
/*
 *   calculate the baseline shift corrected velocity
 *   The velocity will be scaled by a factor of two
 *   to account for the increase in dynamic range that
 *   the baseline shift process requires.
 */
if (vel<(127+BaselineShift))   /* positive value */
        {
         baselineCorrectedVelocity = vel/2;   /* make sure sign bit is not set */
        }
else
        {
         baselineCorrectedVelocity = - (256-vel)/2;   /* output a negative value */
        }
/*      implement b-mode threshold and output corrected velocity
 *      to the lut.
 */
for (b=0; b<BmodeThresh; b++)
        mapptr[(vel<<8)+b] = flag * baselineCorrectedVelocity;
for (b=BmodeThresh; b<256; b++)
        mapptr[(vel<<8)+b] = 0;   /* set color off */
}
}
```

What is claimed is:

1. A method for measuring flow of a fluid in a vessel in a body, comprising the steps of:

producing a value of the velocity of the fluid from a Doppler or time shifted ultrasound signal from each of a plurality of locations on a first scan plane and substantially across the vessel;

obtaining from said velocity values and/or said signal a first averaged velocity value and a first area measurement value;

deriving values for a cross-sectional area of the flow and the averaged velocity of fluid over the cross-sectional area from the averaged velocity value and area measurement value; and calculating from said cross-sectional area of the flow and the averaged velocity of fluid over the cross-sectional area a value of flow of the fluid in the vessel.

2. The method of claim 1, said deriving step including the step of measuring an angle between the first scan plane and the vessel.

3. The method of claim 1, said deriving step including the step of:

repeating the producing and obtaining steps from Doppler or time shifted ultrasound signals from each of a plurality of locations on at least a second scan plane having a different orientation with respect to the vessel than the first scan plane to provide at least a second averaged velocity value and a second area measurement value for said plurality of locations on said at least second scan plane within the vessel.

4. The method of claim 3, said deriving step further including the step of performing a calculation on said first averaged velocity value, said first area measurement value, said at least second averaged velocity value and said at least second area measurement value for said plurality of locations within the vessel.

5. The method of claim 4, said calculation being a least mean square error calculation.

6. The method of claim 3, said producing and obtaining steps including the step of rotationally orienting a scan plane with respect to the vessel to obtain substantially the smallest cross-sectional area of the vessel for a given tilt angle of the transducer to the body.

7. The method of claim 1, said obtaining step including the step of:

providing the total area where there is fluid flow at locations within a region of interest, and an average of the fluid velocities at locations within the region of interest.

8. The method of claim 7, said providing step including the steps of:

acquiring B-mode and/or F-mode data; and identifying locations in the calculation area where there is fluid flow by means of the B-mode and/or F-mode data.

9. The method of claim 8, said identifying step including the step of qualifying the validity of the F-mode data using the B-mode and/or F-mode data.

10. The method of claim 9, wherein the step of qualifying the validity of the F-mode data includes comparing the B-mode data to a preselected threshold value, and rejecting the F-mode data if the B-mode data exceeds said threshold.

11. The method of claim 10, said providing step further comprising determining the area measurement value by counting the qualified F-mode data points that lie within the calculation area.

12. The method of claim 7, said obtaining step further including the step of designating a calculation area in the region of interest, said providing step providing the total area where there is fluid flow at locations within the calculation area, and an average of the fluid velocities at locations within the calculation area.

13. The method of claim 7, said providing step including the steps of:

acquiring scan converted B-mode and/or F-mode data; and identifying locations in the calculation area where there is fluid flow by means of the scan converted B-mode and/or F-mode data.

14. The method of claim 1, wherein said producing step produces a set of values for the velocity of the fluid from Doppler or time shifted ultrasound signals from said plurality of locations during each of a plurality of sampling cycles within one or more heart cycles, and wherein said obtaining step performs an averaging of the velocity values and of the area measurement values over the sampling cycles in one or more complete heart cycles to obtain the averaged velocity value and an averaged area measurement value.

15. The method of claim 1, wherein said producing step produces a set of values for the velocity of the fluid from Doppler or time shifted ultrasound signals from said plurality of locations from multiple frames obtained sequentially within each of a plurality of heart cycles, and wherein said obtaining step performs an averaging of the velocity values and of the area measurement values over a group of frames within each of two or more of said heart cycles to obtain the averaged velocity value and an averaged area measurement value, wherein each group has the same time offset relative to a periodic cardiac event in each of the two or more heart cycles.

16. An apparatus for measuring flow of a fluid in a vessel in a body, comprising:

means for producing a value of the velocity of the fluid from a Doppler or time shifted ultrasound signal from each of a plurality of locations on a first scan plane and substantially across the vessel;

means for obtaining from said velocity values and/or signal an averaged velocity value and an area measurement value;

means for deriving values for the cross-sectional area of the flow and the averaged velocity of fluid over a cross-sectional area from the averaged velocity value and area measurement value; and means for calculating the cross-sectional area of the flow and the averaged velocity of fluid over the cross-sectional area a value of flow of the fluid in the vessel.

17. The apparatus of claim 16, said obtaining means including:

means for providing the total area where there is fluid flow at locations within said calculation area, and an average of the fluid velocities at locations within a calculation area where there is fluid flow.

18. The apparatus of claim 17, said providing means including:

an ultrasound system for acquiring B-mode and/or F-mode data; and means for identifying locations in the calculation area where there is fluid flow by means of the B-mode and/or F-mode data.

19. The apparatus of claim 18, said identifying means including a lookup table for qualifying the validity of the F-mode data using the B-mode and/or F-mode data.

20. The apparatus of claim 17, said obtaining means further including input means for designating a calculation area in the region of interest.

21. The apparatus of claim 17, said providing means including:

an ultrasound system for acquiring scan converted B-mode and/or F-mode data; and means for identifying locations in the calculation area where there is fluid flow by means of the scan converted B-mode and/or F-mode data.

22. The apparatus of claim 16, said producing means producing said value of the velocity of the fluid from said plurality of locations located substantially throughout a cross section of the vessel.

23. The apparatus of claim 16, said producing means producing said value of the velocity of the fluid from said plurality of locations located in a closed cross section of the vessel.

24. The method of claim 1, said producing step producing said value of the velocity of the fluid from said plurality of locations located substantially throughout a cross section of the vessel.

25. The method of claim 1, said producing step producing said value of the velocity of the fluid from said plurality of locations located in a closed cross section of the vessel.

26. A method for measuring flow of a fluid in a vessel in a body using ultrasound equipment, comprising the steps of:

imaging a region of interest that includes an entire cross-sectional area of the vessel by taking data in a first view of the region at a first angle to the vessel and in a second view of the region at a second angle to the vessel;

obtaining a first set of velocity data and a first set of area measurement data for a first plurality of locations within the vessel as imaged in the first view from data obtained in taking the first view;

obtaining a second set of velocity data and a second set of area measurement data for a second plurality of locations within the vessel as imaged in the second view from data obtained in taking the second view; and deducing from said first and second sets of velocity data and from said first and second sets of area measurement at a value of flow of the fluid in the vessel.

27. The method of claim 26, further comprising, in the imaging step, taking the first and second views from a common skin/transducer interface position.

28. The method of claim 26, further comprising, in the imaging step, rotationally orienting a scan plane with respect to the vessel, to obtain substantially the smallest cross-sectional area of the vessel for a given tilt angle of the scan plane to the body.

29. The method of claim 26, wherein the first and second angles to the vessel are independently in the range of from about 15° to about 75°.

30. The method of claim 29, wherein the first and second angles to the vessel are independently in the range of from about 30° to about 60°.

31. The method of claim 26, wherein the imaging step includes obtaining B-mode image data and/or F-mode image data.

32. The method of claim 31, further comprising, in the deducing step, using the B-mode and/or the F-mode data to qualify validity of the F-mode data.

33. The method of claim 32, further comprising the step of qualifying the validity of the F-mode data by comparing the B-mode data to a preselected threshold value, and rejecting the F-mode data if the B-mode data exceeds said threshold.

34. The method of claim 33, further comprising, in the deducing step, determining the first area measurement value by counting the qualified F-mode data points that lie within a region of interest or a designated calculation area.

35. The method of claim 26, further comprising the step of designating a first calculation area for the first view of the image and a second calculation area for the second view of the image.

36. The method of claim 26, each of said obtaining steps including the steps of:

acquiring scan converted B-mode and/or F-mode data; and identifying locations in the calculation area where there is fluid flow by means of the scan converted B-mode and/or F-mode data.

37. A method for measuring flow of a fluid in a vessel in a body, comprising the steps of:

(a) obtaining blood flow parameters from a plurality of locations substantially across the vessel and in a plane;

(b) determining an average velocity of blood flow from said blood flow parameters; and (c) determining a value of cross-sectional area of the vessel in said plane by integrating areas associated with information obtained from ultrasound echoes in the plane (d) using the average velocity and value of cross-sectional area to measure the fluid flow.

38. The method of claim 37, wherein the integrated areas are associated with information obtained from measuring received Doppler or time shifted ultrasound signals.

39. The method of claim 37, wherein the integrated areas are associated with intensity values falling below a threshold for ultrasound echoes from a B-mode scan.

40. The method of claim 37, wherein the integrated areas are associated with intensity values falling above a threshold for ultrasound echoes from a F-mode scan.

41. The method of claim 37, wherein the integrated area is associated with velocity, variance of velocity, or energy parameters.

42. The method of claim 37, wherein the integrating step is executed by counting pixels lying within the cross-sectional area of the vessel and multiplying the result by an area per pixel.

43. The method of claim 42, wherein substantially all the pixels are counted.

44. The method of claim 37, said obtaining step obtaining said blood flow parameters from said plurality of locations located substantially throughout a cross section of the vessel.

45. The method of claim 37, said obtaining step obtaining said blood flow parameters from said plurality of locations located in a closed cross section of the vessel.

46. The method of claim 37, wherein the integrated area is calculated from scan converted intensity values.

47. The method of claim 46, further comprising a step of applying a threshold to said scan converted intensity values before the integrated area is calculated from the thresholded intensity values.

48. The method of claim 47, said applying step qualifying the scan converted intensity values when such values fall below a threshold for ultrasound echoes from a B-mode scan.

49. The method of claim 47, said applying step qualifying the scan converted intensity values when such values fall above a threshold for ultrasound echoes from a F-mode scan.

50. A method for measuring a cross section of flow of a fluid in a vessel in a body, comprising the steps of:

obtaining ultrasound echo information from a plurality of locations located substantially throughout the cross section and in a plane;

scan converting said information; and determining a value of cross-sectional area of the vessel in said plane by integrating areas associated with said scan converted information.

51. A method for measuring a flow parameter of a fluid in a zone such as a vessel in a body, comprising the steps of:

designating a region of interest that encloses said zone;

producing a value of a parameter related to velocity, energy or variance of velocity information of a Doppler or time shifted ultrasound signal from the fluid flow at each of a plurality of locations in an area of the region of interest in the body; and obtaining an averaged value of said parameter over said region.

52. The method of claim 51 wherein said obtaining step comprises the step of:

selecting a plurality of portions of said region of interest where said velocity related parameter meets a predetermined selection criterion.

53. The method of claim 52, further comprising summing the area of said selected plurality of portions where said velocity related parameter meets a predetermined selection criterion to provide an area in said region of interest where there is fluid flow.

54. The method of claim 51, said obtaining step comprising providing an averaged value of said parameter over said selected portions of said region of interest.

55. The method of claim 54, wherein said parameter is velocity of the fluid.

56. The method of claim 55, further comprising multiplying the averaged value of velocity by the selected area of the region where there is fluid flow to obtain an indication of volumetric flow of the fluid.

57. The method of claim 51, said producing step producing said value of the parameter from said plurality of locations located substantially throughout a cross section of the vessel.

58. The method of claim 51, said producing step producing said value of the parameter from said plurality of locations located in a closed cross section of the vessel.

59. A method for measuring a cross section of flow of a fluid in a vessel in a body, comprising the steps of:

obtaining ultrasound Doppler or time shifted information from a plurality of locations substantially across the vessel and in a plane; and determining a value of cross-sectional area of the vessel in said plane by integrating areas associated with said information obtained from said ultrasound Doppler or time shifted information.

60. The method of claim 59, said producing step producing said value of the velocity of the fluid from said plurality of locations located substantially throughout a cross section of the vessel.

61. The method of claim 59, said producing step producing said value of the velocity of the fluid from said plurality of locations located in a closed cross section of the vessel.

* * * * *

UNITED STATES PATENT AND TRADEMARK OFFICE
CERTIFICATE OF CORRECTION

PATENT NO. : 5,623,930
DATED : April 29, 1997
INVENTOR(S) : J. Nelson Wright et al.

It is certified that error appears in the above-indentified patent and that said Letters Patent is hereby corrected as shown below:

<u>In Appendix B</u>

In column 19, line 48, in the line that reads "*   Out 0 . . . v/2 . . . 127baseline Shift/2", after "127" insert --+-- and replace "baseline" with --Baseline--.

In column 19, between lines 55 and 56, line 55 reading as "_____" and line 56 reading as "_____" insert the following line reading --The mapptr is a pointer to the hardware lut RAM page that will be loaded with function B.

In column 19, between lines 56 and 57, line 56 reading as "_____" and line 57 reading as "*   Copyright: Acuson" insert the following lines reading --*   Author: Ismayil Guracar-- and --*   Date: 4/26/95--.

In column 19, line 59, replace "iead" with --load--.

In column 19, line 66, replace "/" with --}--.

In column 19, line 67, replace "*" with --/*--.

In column 19, line 79, replace "in" with --is--.

In column 21, line 17, delete "implement b-mode threshold and output corrected velocity" after "/*   ".

UNITED STATES PATENT AND TRADEMARK OFFICE
CERTIFICATE OF CORRECTION

PATENT NO. : 5,623,930
DATED : April 29, 1997
INVENTOR(S) : J. Nelson Wright et al.

It is certified that error appears in the above-indentified patent and that said Letters Patent is hereby corrected as shown below:

In Appendix B (cont'd)

In column 21, between lines 17 and 18, line 17 reading as "/*     implement b-mode threshold and output corrected velocity" and line 18 reading as "*     to the lut" insert --*     implement b-mode threshold and output corrected velocity--.

In the Claims

In Claim 26, line 17, replace "at" with --data--.

In Claim 41, line 1, replace "area" with --areas--.

In Claim 41, line 2, replace "is" with --are--.

Signed and Sealed this

Twentieth Day of April, 1999

Attest:

Q. TODD DICKINSON

*Attesting Officer*     Acting Commissioner of Patents and Trademarks